United States Patent
Chin

(10) Patent No.: US 12,280,095 B2
(45) Date of Patent: Apr. 22, 2025

(54) TISSUE MODIFIER AND USES THEREFOR

(71) Applicant: Fibrosoft Pte Ltd, Orchard (SG)

(72) Inventor: David Chin, Auchenflower (AU)

(73) Assignee: Fibrosoft Pte Ltd, Orchard (SG)

( * ) Notice: Subject to any disclaimer, the term of this patent is extended or adjusted under 35 U.S.C. 154(b) by 0 days.

(21) Appl. No.: 18/555,377

(22) PCT Filed: Aug. 25, 2022

(86) PCT No.: PCT/AU2022/051003
§ 371 (c)(1),
(2) Date: Oct. 13, 2023

(87) PCT Pub. No.: WO2023/023776
PCT Pub. Date: Mar. 2, 2023

(65) Prior Publication Data
US 2024/0197840 A1    Jun. 20, 2024

(30) Foreign Application Priority Data

Aug. 25, 2021  (AU) .................. 2021902736

(51) Int. Cl.
| | | |
|---|---|---|
| A61P 11/08 | (2006.01) | |
| A61K 31/513 | (2006.01) | |
| A61K 31/58 | (2006.01) | |
| A61K 38/47 | (2006.01) | |
| A61K 38/48 | (2006.01) | |

(52) U.S. Cl.
CPC .......... *A61K 38/482* (2013.01); *A61K 31/513* (2013.01); *A61K 31/58* (2013.01); *A61K 38/47* (2013.01); *C12Y 302/01035* (2013.01); *C12Y 304/21068* (2013.01)

(58) Field of Classification Search
CPC ............... A61P 35/00; C07K 14/4705; C12Y 302/01035; C12Y 304/21068; C12Y 304/21073; A61Q 19/00
USPC ...................................... 424/94.62
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,524,065 A | 6/1985 | Pinnell |
| 4,645,668 A | 2/1987 | Pinnell |
| 4,837,028 A | 6/1989 | Allen |
| 5,019,369 A | 5/1991 | Presant et al. |
| 2014/0323930 A1 | 10/2014 | Edwards |
| 2016/0000890 A1 | 1/2016 | Yu et al. |
| 2016/0331817 A1 | 11/2016 | Raven |
| 2016/0331917 A1 | 11/2016 | Bennett et al. |

FOREIGN PATENT DOCUMENTS

| | | |
|---|---|---|
| CN | 105412918 A | 3/2016 |
| WO | 0030578 A1 | 6/2000 |
| WO | 2010102262 A1 | 9/2010 |
| WO | 2012155212 A1 | 11/2012 |
| WO | 2021076792 A1 | 4/2021 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Danilkovitch-Miagkova et al., "Hyaluronidase 2 Negatively Regulates RON Receptor Tyrosine Kinase and Mediates Transformation of Epithelial Cells by Jaagsiekte Sheep Retrovirus", Proc. Natl. Acad. Sci. USA, vol. 100, No. 8, 2003, pp. 4580-4585.
Abstract of Frost, I.G. et al., "A Microtiter-Based Assay for Hyaluronidase Activity Not Requiring Specialized Reagents", Anal. Biochemistry, vol. 251, 1997, 4 pages.
Abstract of Frost, I.G. et al., "Purification, Cloning and Expression of Human Plasma Hyaluronidase", Biochem. Biophy. Res. Commun., vol. 236, No. 1, 1997, 4 pages.
George, Jacob et al., "In Vivo Inhibition of Rat Stellate Cell Activation by Soluble Transforming Growth Factor ? Type II Receptor: A Potential New Therapy for Hepatic Fibrosis", Proc Natl Acad Sci USA, vol. 96, No. 22, 1999, pp. 12719-12724.
International Search Report for Application No. PCT/AU2022/051003 dated Oct. 25, 2022, 5 pages.
Lalancette, Claudia et al., "Characterization of an 80-Kilodalton Bull Sperm Protein Identified as PH-20", Biol Reprod., vol. 65, No. 2, 2001, pp. 628-636.

(Continued)

*Primary Examiner* — Robert B Mondesi
*Assistant Examiner* — Mohammad Y Meah
(74) *Attorney, Agent, or Firm* — Howard & Howard Attorneys PLLC

(57) ABSTRACT

Disclosed are compositions, methods, uses, kits and articles of manufacture, which are based on the use of a hyaluronidase and a collagen-reducing agent, for reducing or inhibiting the development of fibrosis in a tissue, or for treating collagen-mediated disorders. In specific embodiments, the collagen-mediated disorders are fibroproliferative disorders involving alterations of collagen, including fibromatoses such as Dupuytren's disease. Peyronie's disease and Ledderhose's disease.

26 Claims, 7 Drawing Sheets

(56) References Cited

OTHER PUBLICATIONS

Limmer, E.E. et al., "A Review of Current Keloid Management: Mainstay Monotherapies and Emerging Approaches", Dermatology and Therapy, vol. 10, No. 5, Oct. 2020, pp. 931-948.

Phelps, Bonnie et al., "Restricted Lateral Diffusion of PH-20, a PI-Anchored Sperm Membrane Protein", Science, vol. 240, No. 4860, 1988, pp. 1780-1782.

Qi et al., "Blockade of Type ? Transforming Growth Factor Signaling Prevents Liver Fibrosis and Dysfunction in the Rat", Proc Natl Acad Sci USA, vol. 96, No. 5, 1999, pp. 2345-2349.

Abstract of Stahl, P.H. et al., "Pharmaceutical Salts: Properties, Selection, and Use", Journal of Pharmaceutical Science, vol. 66, 1977, 3 pages.

Baley-Spindel, MD, Isaac et al., "Perivascular Hyaluonidase with Alteplase as Treatment for Hyaluronic Acis Thrombosis", Aesthetic Surgery Journal, vol. 40, No. 5, Apr. 8, 2019, pp. 551-559.

Chiang, M.D., ChengAn et al., "Introverts Hyaluronidase with Urokinase as Treatment for Rabbit Retinal Artery Hyaluronic Acid Embolism", Plastic and Reconstructive Surgery, vol. 137, No. 1, Jan. 1, 2016, pp. 114-121.

Dehaas, WHD, "Dupuytren'Disease: Treatment with Local in jections of Hyaluronidase Using the Dermojet", ACTA Rhumatol., vol. 3, No. 4, Jan. 1, 1979, pp. 275-285.

English language abstract and machine-assisssted English translation for CN 105412918 A extracted from espacenet.com database on Mar. 5, 2025, 6 pages.

\* cited by examiner

A

B

C

D

A

B

C

D

A

B

C

D

E

F

A

B

C

D

A

B

TISSUE MODIFIER AND USES THEREFOR

CROSS-REFERENCE TO RELATED APPLICATIONS

This application is the National Stage of International Patent Application No. PCT/AU2022/051003, filed on Aug. 25, 2022, which claims priority to Australian Provisional Application No. 2021902736 entitled "Tissue Modifier and Uses Therefor" filed 25 Aug. 2021, the contents of which are incorporated herein by reference in their entirety.

FIELD

The present disclosure relates generally to compositions, methods, uses, kits and articles of manufacture, which are based on the use of a hyaluronidase and a collagen-reducing agent, for reducing or inhibiting the development of fibrosis in a tissue, or for treating collagen-mediated disorders. In specific embodiments, the collagen-mediated disorders are fibroproliferative disorders involving alterations of collagen, including fibromatoses such as Dupuytren's disease, Peyronie's disease and Ledderhose's disease.

BACKGROUND

Fibrosis of tissue is caused by excessive production and accumulation in tissue of extracellular matrix, which is mainly collagen. When tissue is damaged by a stimulus such as oxidative stress, hypoxia, inflammation, or apoptosis, damaged tissue is repaired by replacement with extracellular matrix, but in the case of the damage being serious or in the case of such stimulation becoming chronic, the accumulation of extracellular matrix becomes excessive, leading to disfiguring deposits of new tissue and undermining normal function of the tissue. The excess collagen deposition has been attributed to a disturbance in the balance between collagen synthesis and collagen degradation, and it is thought that collagen-producing cells such as fibroblasts including fasciacytes and myofibroblasts give rise to the disease state.

Numerous diseases and conditions are associated with excess collagen deposition and the erratic accumulation of fibrous tissue rich in collagen. Such diseases and conditions are collectively referred to herein as "collagen-mediated disorders", including fibroproliferative disorders, which are characterized by excessive connective tissue accumulation and slow, but continuous, tissue contraction that lead to progressive deterioration in the normal structure and function of the affected organ(s). Representative examples of fibroproliferative disorders include idiopathic pulmonary fibrosis, hepatic cirrhosis, myelofibrosis, systemic sclerosis, hypertrophic scars, keloids, Ledderhose's disease, frozen shoulder syndrome, Dupuytren's disease, and Peyronie's disease.

Dupuytren's disease (also known as Dupuytren's contracture, morbus Dupuytren or palmar fascial fibromatosis) is a fascial fibromatosis characterized by the buildup of extracellular matrix materials such as collagen on the connective tissue of the hand (the palmar fascia) causing it to form nodules in the palmar and digital fascia. The nodules eventually grow into cords of contracted tissue which gradually pull one or more of the sufferer's fingers towards their palm resulting in the finger adopting a permanently flexed position.

The underlying cause of Dupuytren's disease is not well understood. It is believed that the disease develops in three stages whereby, in the first stage, a proliferation of myofibroblast cells is observed. In the second stage, the myofibroblasts align along lines of tension in the fascia leading to the third stage wherein the affected tissue becomes mostly acellular and only thick bands of collagen remain. Studies have shown that these bands show a high ratio of type III to type I collagen which is in contrast to the predominantly type I collagen found in normal palmar fascia.

Dupuytren's disease is a relatively common condition with its prevalence varying in different populations. Over 30 percent of Northern European males may be affected at 50 years old and 40 percent for those 80 years and older. It has a negative effect on a patient's quality of life, since, once contracture reaches an advanced stage, they find themselves unable to perform simple tasks requiring fine control of the fingers.

Treatment of Dupuytren's disease has traditionally been invasive surgical techniques. Traditionally, the treatment has involved surgical excision of the offending tissue. In severe or recurrent disease, the surgical excision may be combined with excision of the overlying palmar skin and resurfacing of the cutaneous defect with full-thickness skin graft. Surgery is typically followed by prolonged rehabilitation, usually lasting 3 months and complications have been reported in up to 20% of cases. Such surgical correction is the mainstay treatment of later stage disease when secondary changes to tendons and joints have developed. A less invasive surgical intervention is needle fasciotomy in which the fibrous bands (contractures) in connective tissue are divided using the bevel of a needle. Nevertheless, there are concerns regarding this type of surgical procedure including the risk of nerve or artery damage as well as postoperative infection.

Peyronie's disease (also known as penile fascial fibromatosis) and Ledderhose's disease (also known as plantar fascial fibromatosis) are considered to be related diseases to Dupuytren's disease due to the similar underlying collagen and connective tissue accumulation. Peyronie's disease is a connective tissue disorder involving the growth of fibrous plaques in the soft tissue of the penis which may result in an abnormal curvature. It has been reported that approximately 30% of men who suffer from Peyronie's disease will also develop fibrosis in other parts of the body such as the hand (Dupuytren's disease) or the foot (Ledderhose's disease). Ledderhose's disease is a non-malignant thickening of the feet's deep connective tissue. In the initial stages of the disease nodules or cords start growing along tendons of the foot (in the same manner as occurs in Dupuytren's disease) which may become tender. Eventually the cords thicken, the toes stiffen and bend and walking becomes extremely painful. It has been found that the histological and ultrastructural features of Ledderhose's and Dupuytren's disease are the same and so it is believed they have a common etiology and pathogenesis. Effective treatments for Ledderhose's disease are currently not available as surgery can worsen the condition with further plantar fascia thickening and formation of nodules causing further discomfort for the patient and post-operative rehabilitation is relatively long and painful.

Although surgical intervention has always been the method of choice in the treatment of fibroproliferative disorders such as Dupuytren's disease and Peyronie's disease, non-surgical treatments have recently become available.

For example, intralesional injection of collagenase *Clostridium histolyticum* (CCH) (marketed under Xiaflex™ in the United States and Xiapex™ in Europe) is clinically approved for non-surgical treatment of v disease and Peyronie's disease. Clinical trials have shown that CCH has significant efficacy over placebo in reducing contractures and increasing range of motion in Dupuytren's disease patients and in reducing penile curvature in Peyronie's disease patients. The cost of this drug, however, is relatively high, which is a significant drawback to affected patients when a treatment course involves multiple injections over several months.

Other collagen-reducing agents have been contemplated for non-surgical treatment of fibroproliferative disorders including the use of activators of collagenase production pathway. For example, WO2012/155212 discloses intralesional injection of plasminogen activator for converting endogenous plasminogen to plasmin, which in turn mediates conversion of pro-collagenase to collagenase. The endogenously produced collagenase then facilitates treatment of the fibromatotic lesion. Plasminogen activators have several advantages over CCH, including cheaper cost and less inflammatory side effects.

The incidence of adverse fibroproliferative disorders is remarkably high. For example, it is estimated that 4-6% of the world population suffers from Dupuytren's disease. Within the US alone, approximately 25% of middle age persons and greater than 32% of over 50 year olds are afflicted to varying extents. In other countries, approximately 20% of males over 50 years old and greater than 80% of over 80 year olds in Germany are affected compared to 17-35% of the Australian population. In addition, with the incidence of diabetes on the increase, at least in the western world, a correlation has been observed between diabetes and a higher incidence of Dupuytren's disease. Compounding this is the direct correlation between patients on anticoagulants and fibroproliferative disorders.

There remains a need for improvements in the treatment of fibromatoses and other fibroproliferative disorders.

SUMMARY

The present disclosure is based in part on the surprising determination that co-administration of a collagen-reducing agent and a hyaluronidase locally to a site of disease associated with a collagen-mediated disorder, including a fibroproliferative disorder (e.g., a fibromatosis), markedly improves the treatment of the collagen-mediated disorder, as compared to treatment with the collagen-reducing agent alone. Notably, hyaluronidase was found to significantly reduce the mean time required to observe discernible reduction in volume of fibromatosis, reduction of contracture and improvement in the range of motion in patients with Dupuytren's disease, from about 4-6 weeks to about 2-3 days. This striking improvement in treatment efficacy is advantageous as it leads to faster beneficial outcomes for patients with collagen-mediated disorders such as fibroproliferative disorders such as fibromatoses, including earlier improvement or restoration of organ function and return to work. Additionally, the present inventor has found that local co-administration of hyaluronidase to the site of disease significantly reduces the force and work required for injection of the collagen-reducing agent into a fibromatosis lesion, leading to better physician control of an injector needle, more effective intralesional dispersion of the collagen-reducing agent, as well as improved patient safety and comfort.

Accordingly, disclosed herein in one aspect are methods for reducing or inhibiting the development of fibrosis in a tissue, suitably in a subject in need thereof. These methods generally comprise, consist or consist essentially of contacting the tissue with a collagen-reducing agent and a hyaluronidase, to thereby reduce or inhibit the development of fibrosis in the tissue. The reduction or inhibition of fibrosis in the tissue is suitably associated with at least one of: reduction in the size or volume of the fibrosis; remodeling of the fibrosis or tissue, including shrinkage of the fibrosis, degradation of the fibrosis, modulation of the viscoelastic properties of the tissue, softening of the tissue, relaxation of the tissue and/or stretching of the tissue; and elimination of at least a portion the fibrosis in the tissue.

The collagen-reducing agent may be a collagen degradation agent, a suppressor of collagen production by collagen-producing cells, or a suppressor of a collagen degradation inhibitor. In some embodiments, the collagen-reducing agent is a collagen degradation agent, representative examples of which include collagenases (e.g., bacterial collagenases such as *Clostridium histolyticum* (CCH); and mammalian matrix metalloproteinases (MMP) such as MMP1, MMP2, MMP3, MMP7, MMP8, MMP9, MMP10, MMP11, MMP12, MMP13, and MMP14) and collagenase-producing agents (e.g., plasminogen; plasminogen activators such as tissue plasminogen activator (tPA) and urokinase type plasminogen activator (uPA), kallikrein, Factor XII, a nucleic acid molecule from which a plasminogen, plasminogen activator, kallikrein, or Factor XII is expressible, or a cell comprising such a nucleic acid molecule).

The hyaluronidase may be animal-derived or recombinantly-produced. In some embodiments, the hyaluronidase is selected from Amphadase, Hyalase, Hydase, Hylase, rHuPH20/Hylenex, Vitrase and Wydase.

The methods may further comprise contacting the tissue with at least one ancillary anti-fibrotic agent. The ancillary anti-fibrotic agent(s) may be selected from steroids and antimetabolites.

Illustrative steroids include corticosteroids, representative examples of which include prednisone, prednisolone, methylprednisolone, beclomethasone, betamethasone, dexamethasone, fludrocortisone, hydrocortisone, triamcinolone, their derivatives, prodrugs and pharmaceutically acceptable salts, and combinations thereof. In certain embodiments, the steroid is triamcinolone, a triamcinolone derivative, a triamcinolone prodrug, or a pharmaceutically acceptable salt thereof.

Representative antimetabolites include pyrimidine antagonists, folic acid antagonists, purine antagonists and deaminase inhibitors. In some embodiments, the antimetabolite is selected from 5-fluorouracil, foxuridine, cytarabine, capecitabine, gemcitabine, 6-mercaptopurine, 6-thioguanine, cladribine, fludarabine, nelarabine and pentostatin, their derivatives and pharmaceutically acceptable salts, and combinations thereof. In certain embodiments, the antimetabolite is 5-fluorouracil, a 5-fluorouracil derivative, a 5-fluorouracil prodrug, or a pharmaceutically acceptable salt thereof.

In a related aspect, methods are disclosed for treating a collagen-mediated disorder, including a fibroproliferative disorder such as a fibromatosis, in a subject. These methods generally comprise, consist or consist essentially of administering to the subject a collagen-reducing agent and a hyaluronidase in effective amounts to treat the collagen-mediated disorder, wherein the collagen-reducing agent and hyaluronidase are co-administered to a site of disease associated with the collagen-mediated disorder, or a site of manifestation of symptom thereof.

The amounts of collagen-reducing agent and hyaluronidase are suitably effective for reducing the size or volume, shrinking, degrading, changing the viscoelastic properties of, softening, relaxing, stretching, or eliminating at least a portion of, a fibrotic lesion associated with the collagen-mediated disorder. In specific embodiments, the collagen-reducing agent and hyaluronidase are administered in synergistically effective amounts.

The treatment methods disclosed herein may further comprise co-administering to the subject at least one ancillary anti-fibrotic agent selected from a steroid and an antimetabolite as broadly described above and elsewhere herein.

In some embodiments, the collagen-mediated disorder is a fibroproliferative disorder, representative examples of which include hypertrophic scar, hyperplastic scar, keloid scar, liver fibrosis, lung fibrosis, skin fibrosis, muscle fibrosis, kidney fibrosis, glomerulosclerosis, uterine fibrosis, radiation fibrosis and fibromatoses. In specific embodiments, the fibroproliferative disorder is a fibromatosis, representative examples of which include adhesive capsulitis, Peyronie's disease, Dupuytren's disease and Ledderhose's disease.

The local administration of the collagen-reducing agent and hyaluronidase is suitably by local injection (e.g., intralesional injection, subdermal injection, etc.).

In some embodiments, the methods further comprise administering to the subject an adjunctive surgical treatment, illustrative examples of which include surgical fasciectomy, surgical fasciotomy, surgical dermofasciectomy and needle fasciotomy.

Disclosed herein in another aspect is the use of a collagen-reducing agent and a hyaluronidase, optionally in combination with at least one ancillary anti-fibrotic agent that is suitably selected from a steroid and an antimetabolite, in the manufacture of a medicament for reducing or inhibiting the development of fibrosis in a tissue, or for treating a collagen-mediated disorder (e.g., a fibroproliferative disorder such as a fibromatosis).

Yet another aspect of the present disclosure extends to the use of a hyaluronidase for enhancing the treatment efficacy of a collagen-reducing agent, optionally in combination with at least one ancillary anti-fibrotic agent that is suitably selected from a steroid and an antimetabolite, for reducing or inhibiting the development of fibrosis in a tissue, or for treating a collagen-mediated disorder (e.g., a fibroproliferative disorder such as a fibromatosis).

Still another aspect of the present disclosure encompasses the use of a hyaluronidase, optionally in combination with at least one ancillary anti-fibrotic agent that is suitably selected from a steroid and an antimetabolite, for enhancing the efficacy of a collagen-reducing agent for reducing or inhibiting the development of fibrosis in a tissue, or for treating a collagen-mediated disorder (e.g., a fibroproliferative disorder such as a fibromatosis).

In any of the aspects disclosed herein the collagen-reducing agent and hyaluronidase are suitably formulated for local administration to a site of disease (e.g., lesion) associated with the collagen-mediated disorder (e.g., a fibroproliferative disorder such as a fibromatosis), or a site of manifestation of symptom thereof. The at least one ancillary anti-fibrotic agent (e.g., steroid and/or an antimetabolite) may be independently formulated for local administration or systemic administration (e.g., orally, parenterally, intravenously, intradermally, subcutaneously, or topically, including transdermally).

Disclosed herein in another aspect are kits comprising a first medicament comprising a hyaluronidase, an optional pharmaceutically acceptable carrier, and a package insert comprising instructional material for co-administration of the first medicament with a second medicament comprising a collagen-reducing agent and an optional pharmaceutically acceptable carrier for reducing or inhibiting the development of fibrosis in a tissue, or for treating a collagen-mediated disorder (e.g., a fibroproliferative disorder such as a fibromatosis), or for enhancing the efficacy of a collagen-reducing agent for reducing or inhibiting the development of fibrosis in a tissue, or for treating a collagen-mediated disorder (e.g., a fibroproliferative disorder such as a fibromatosis), wherein the first medicament and second medicament are formulated for co-administration to a site of disease associated with the collagen-mediated disorder, or a site of manifestation of symptom thereof. In some embodiments, the package insert comprises instructional material for co-administration of the first and second medicaments with at least one other medicament comprising an ancillary anti-fibrotic agent that is suitably selected from a steroid and an antimetabolite and an optional pharmaceutically acceptable carrier.

In a related aspect, the present disclosure provides kits comprising a first medicament comprising a hyaluronidase and an optional pharmaceutically acceptable carrier, and a second medicament comprising a collagen-reducing agent and an optional pharmaceutically acceptable carrier for reducing or inhibiting the development of fibrosis in a tissue, or for treating a collagen-mediated disorder (e.g., a fibroproliferative disorder such as a fibromatosis). In some embodiments, the kits further comprise a package insert comprising instructional material for co-administering the first medicament and the second medicament for reducing or inhibiting the development of fibrosis in a tissue, or for treating a collagen-mediated disorder (e.g., a fibroproliferative disorder such as a fibromatosis), wherein the first medicament and second medicament are formulated for co-administration to a site of disease associated with the collagen-mediated disorder, or a site of manifestation of symptom thereof. In some embodiments, the package insert comprises instructional material for co-administration of the first and second medicaments with at least one other medicament comprising an ancillary anti-fibrotic agent that is suitably selected from a steroid and an antimetabolite and an optional pharmaceutically acceptable carrier.

In another related aspect, kits are provided comprising a first medicament comprising a hyaluronidase and an optional pharmaceutically acceptable carrier, a second medicament comprising a collagen-reducing agent and an optional pharmaceutically acceptable carrier for reducing or inhibiting the development of fibrosis in a tissue, or for treating a collagen-mediated disorder (e.g., a fibroproliferative disorder such as a fibromatosis), and at least one other medicament comprising an ancillary anti-fibrotic agent and an optional pharmaceutically acceptable carrier, wherein the ancillary anti-fibrotic agent is suitably selected from a steroid and an antimetabolite, wherein the first and second medicaments are formulated for co-administration to a site of disease associated with the collagen-mediated disorder, or a site of manifestation of symptom thereof, and wherein the at least one other medicament is formulated for co-administration with the first and second medicaments. In some embodiments, the kits further comprise a package insert comprising instructional material for co-administering the first medicament, second medicament and the at least one other medicament for treating the collagen-mediated disorder.

When the kits of the present disclosure comprise multiple medicaments, some or all of the medicaments may be provided in a single composition or in separate compositions. The collagen-reducing agent, hyaluronidase and/or ancillary anti-fibrotic agent-containing compositions are suitably in liquid form.

In any of the aspects and embodiments disclosed herein, the collagen-reducing agent is preferably a collagenase-producing agent.

Disclosed herein in another aspect are pharmaceutical compositions for reducing or inhibiting the development of fibrosis in a tissue, or for treating a collagen-mediated disorder (e.g., a fibroproliferative disorder such as a fibromatosis). These compositions generally comprise, consist or consist essentially of a collagenase-producing agent and a hyaluronidase. The collagenase-producing agent may be selected from plasminogen activators such as tissue plasminogen activator (tPA) and urokinase type plasminogen activator (uPA), plasminogen, kallikrein, Factor XII, a nucleic acid molecule from which a plasminogen activator, plasminogen, kallikrein, Factor XII, or a collagenase is expressible, or a cell comprising such a nucleic acid molecule.

The collagenase-producing agent and hyaluronidase are suitably in effective amounts to facilitate at least one of: reducing the size or volume of the fibrosis or the fibrotic tissue; remodeling of the fibrosis or the fibrotic tissue associated with the collagen-mediated disorder, including shrinkage of the fibrosis or the fibrotic tissue associated with the collagen-mediated disorder, degradation of the fibrosis or the fibrotic tissue associated with the collagen-mediated disorder, modulation of the viscoelastic properties of the fibrosis or the fibrotic tissue associated with the collagen-mediated disorder, softening of the fibrotic tissue associated with the collagen-mediated disorder, relaxation of the fibrotic tissue associated with the collagen-mediated disorder, and/or stretching of the fibrotic tissue associated with the collagen-mediated disorder; and elimination of at least a portion the fibrotic tissue associated with the collagen-mediated disorder.

In some embodiments, the collagenase-producing agent is a plasminogen activator such as tissue plasminogen activator (tPA) or a urokinase type plasminogen activator (uPA). The plasminogen activator may be present in the composition at a concentration of about $1\times10^4$ U/mL to about $1\times10^7$ U/mL (and all integer concentrations in between).

In related embodiments, the plasminogen activator is in an amount corresponding to about $1\times10^5$ U to about $1\times10^8$ U (and all integer units in between) per single unit dose.

In other related embodiments, the plasminogen activator is in an amount of about 0.1 mg to about 200 mg (and all one-tenth milligram units in between) per single unit dose.

The hyaluronidase may be present in the composition at a concentration of about 1 U/mL to about $2\times10^3$ U/mL (and all integer concentrations in between).

In related embodiments, the hyaluronidase is in an amount corresponding to about 10 U to about $2\times10^4$ U (and all integer units in between) per single unit dose.

In other related embodiments, the hyaluronidase is in an amount of about 0.01 mg to about 20 mg (and all one-hundredth milligram units in between) per single unit dose.

In some embodiments, the molar ratio of plasminogen activator to hyaluronidase in the composition is from about 50:1 to 5:1 (and all integer ratios in between).

The compositions may further comprise one or both of a steroid and an antimetabolite as broadly described above and elsewhere herein.

The steroid is preferably a corticosteroid, representative examples of which include prednisone, prednisolone, methylprednisolone, beclomethasone, betamethasone, dexamethasone, fludrocortisone, hydrocortisone, triamcinolone, or their derivatives, prodrugs and pharmaceutically acceptable salts, and combinations thereof. The corticosteroid (e.g., triamcinolone, a triamcinolone derivative, a triamcinolone prodrug or a pharmaceutically acceptable salt thereof) may be present in the composition at a concentration of about 0.1 mg/ml to about 60 mg/mL (and all one-tenth unit concentrations in between).

In specific embodiments, the corticosteroid (e.g., triamcinolone, a triamcinolone derivative, a triamcinolone prodrug or a pharmaceutically acceptable salt thereof) may be present in the composition in an amount of about 1 mg to about 600 mg (and all integer milligram units in between) per single unit dose.

In some embodiments, the molar ratio of hyaluronidase to corticosteroid (e.g., triamcinolone, a triamcinolone derivative, a triamcinolone prodrug or a pharmaceutically acceptable salt thereof) in the composition is from about 1:100000 to 1:10000 (and all integer ratios in between).

The antimetabolite may be selected from a pyrimidine antagonist, a folic acid antagonist, a purine antagonist or a deaminase inhibitor. In specific embodiments, the antimetabolite is suitably selected from 5-fluorouracil, foxuridine, cytarabine, capecitabine, gemcitabine, 6-mercaptopurine, 6-thioguanine, cladribine, fludarabine, nelarabine and pentostatin, or their derivatives, prodrugs and pharmaceutically acceptable salts, and combinations thereof. In representative embodiments, the antimetabolite (e.g., 5-fluorouracil, a 5-fluorouracil derivative, a 5-fluorouracil prodrug, or a pharmaceutically acceptable salt thereof) is present in the composition at a concentration of about 0.01 mg/mL to about 5 mg/ml (and all integer concentrations in between).

In specific embodiments, the antimetabolite (e.g., 5-fluorouracil, a 5-fluorouracil derivative, a 5-fluorouracil prodrug, or a pharmaceutically acceptable salt thereof) may be present in the composition in an amount of about 0.1 mg to about 50 mg (and all one-tenth milligram units in between), about 0.2 mg to about 40 mg (and all one-tenth milligram units in between), about 0.4 mg to about 30 mg (and all one-tenth milligram units in between), about 0.6 mg to about 20 mg (and all one-tenth milligram units in between), about 0.8 mg to about 16 mg (and all one-tenth milligram units in between), about 1 mg to about 12 mg (and all one-tenth milligram units in between), or about 2 mg to about 10 mg (and all one-tenth milligram units in between) per single unit dose.

In some embodiments, the molar ratio of hyaluronidase to antimetabolite (e.g., 5-fluorouracil, a 5-fluorouracil derivative, a 5-fluorouracil prodrug, or a pharmaceutically acceptable salt thereof) in the composition is from about 1:10000 to 1:1000 (and all integer ratios in between).

The compositions may comprise a pharmaceutically acceptable carrier.

The compositions may be in the form of a liquid composition (e.g., a subdermal or intralesional liquid composition). Suitably, the compositions are formulated for direct injection into a tissue associated with fibrosis or fibrotic lesion associated with the collagen-mediated disorder. In some embodiments, the compositions are formulated for subdermal, preferably intralesional administration.

The compositions may further comprise a buffering agent suitable to adjust the pH of the composition to a pH of about 5 to 8. In representative examples of this type, the buffering agent is suitable to adjust the pH of the composition to one approximating physiological blood. Generally, the buffering agent is an alkaline buffering agent, which in certain embodiments, is selected from sodium bicarbonate, magnesium bicarbonate and calcium bicarbonate.

Still another aspect of the present disclosure provides articles of manufacture for reducing or inhibiting the development of fibrosis in a tissue, or for treating a collagen-mediated disorder (e.g., a fibroproliferative disorder such as a fibromatosis). These articles of manufacture generally comprise, consist or consist essentially of a pharmaceutical composition as broadly described above and elsewhere herein. In some embodiments, the article of manufacture is a single use vial or syringe.

In any of the aspects and embodiments broadly described above and elsewhere herein, the disclosed methods, uses, kits and pharmaceutical compositions are preferably for use in treating a fibromatosis including, for example, a palmar fibromatosis (Dupuytren's disease), a penile fibromatosis (Peyronie's disease), a plantar fibromatosis (Ledderhose's disease), a desmoid fibromatosis (e.g., abdominal fibromatosis) and adhesive capsulitis (frozen shoulder).

DETAILED DESCRIPTION

1. Definitions

Figure 1:
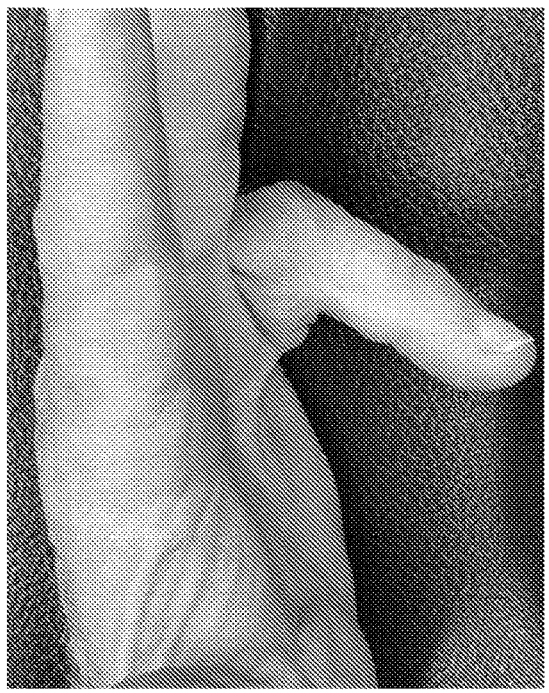
FIG. 1 is a photographic representation showing the results of treating a Dupuytren's disease patient with an embodiment of the composition of the present disclosure. A. Side view of the patient's contracted finger is shown prior to treatment with the composition. B. Frontal view of the patient's contracted finger is shown prior to treatment with the composition. C. Side view of the patient's finger is shown two days after intralesional injection of the composition. D. Frontal view of the patient's finger is shown two days after intralesional injection of the composition. At least a 30-degree improvement in flexion of the diseased finger was obtained using this treatment.
Figure 1:
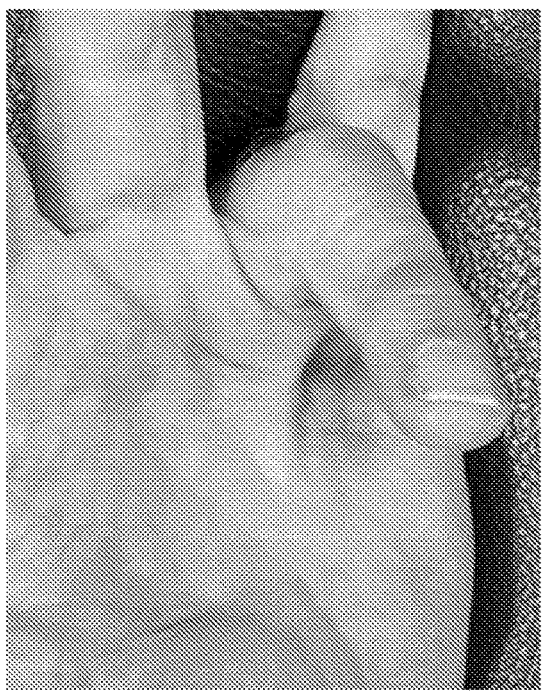
Figure 1:
Figure 1:
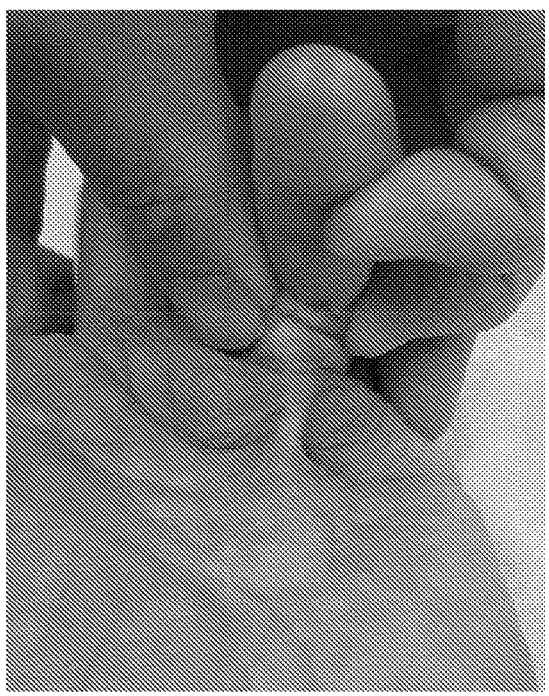

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

The term "about" as used herein refers to the usual error range for the respective value readily known to the skilled person in this technical field. Reference to "about" a value or parameter herein includes (and describes) embodiments that are directed to that value or parameter per se. In specific embodiments, the term "about" refers to a value or parameter (e.g., quantity, level, concentration, number, frequency, percentage, dimension, size, amount, weight or length) that varies by as much 15, 14, 13, 12, 11, 10, 9, 8, 7, 6, 5, 4, 3, 2 or 1% to a reference value or parameter.

The term "administration" refers to systemic and/or local administration. The term "systemic administration" refers to non-localized administration, for example enteral or parenteral, such that an administered substance may affect several organs or tissues throughout the body or such that an administered substance may traverse several organs or tissues throughout the body in reaching a target site. Suitable forms of systemic administration, in part, depend upon the use or the route of entry, for example oral, transdermal or by injection. The term "oral administration" used herein refers to the administration of compound via the mouth through ingestion, or via some other part of the gastrointestinal system including the esophagus. The term "parenteral administration" refers to and includes any route through which as substance is administered other than through the digestive tract, non-limiting examples of such routes include: intravenous injection, intra-arterial injection, intra-muscular injection, and injection through an intravenous line, cannula, catheter, and the like. Typically, "local administration" refers to administration of agent into a limited, or circumscribed, anatomic space, such as subcutaneous (s.c.) injections and intramuscular (i.m.) injections. This term also includes within its scope a route of administration in which an agent is delivered to a site that is apposite or proximal, e.g., within about 10 cm, or direct administration (e.g., direct injection) to the site of the lesion or disease. The term "local administration excludes" systemic routes of administration such as intravenous administration or oral administration. The terms "topical application" and "topically applied" are used interchangeably herein to refer to the application onto the outer layer of mammalian skin, which include application by rubbing onto the skin, brushing, painting, wiping and stroking. Suitable pharmaceutical compositions for topical administration may, for example, comprise ointments, creams, aqueous or oily solutions or suspensions transdermal patches, films, gels, lotions and the like.

The term "agent" includes any substance that induces a desired pharmacological and/or physiological effect. This term encompasses the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and nucleic acid molecules such as RNA, DNA and mimetics and chemical analogs thereof as well as cellular agents. Thus, the term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

As used herein, an "amount" of a compound as measured in milligrams refers to the milligrams of compound present in a composition, regardless of the form of the composition. For example, an "amount of compound which is 10 mg" means the amount of the compound in a preparation is 10 mg, regardless of the form of the preparation. Thus, when in the form with a carrier, the weight of the composition necessary to provide a dose of 10 mg compound would be greater than 10 mg due to the presence of the carrier.

As used herein, "and/or" refers to and encompasses any and all possible combinations of one or more of the associated listed items, as well as the lack of combinations when interpreted in the alternative (or).

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The term "anti-fibrotic agent" refers to a substance that has anti-fibrotic activity (i.e., prevents or reduces fibrosis) in a subject. This takes into account the abnormal formation of fibrous connective tissue, which is typically comprised of collagen. These substances may have different mechanisms of action, some reducing the formation of collagen or another protein, others enhancing the catabolismor removal of collagen in the affected area of the body. All such substances having activity in the reduction of the presence of fibrotic tissue are included herein, without regard to the particular mechanism of action by which each such drug functions.

The term "antimetabolite" is used herein to refer to a therapeutic agent that inhibits utilization of a naturally occurring metabolite in normal metabolism. Generally, the therapeutic agent is structurally similar to a critical natural intermediate (metabolite) in a biochemical pathway leading to DNA or RNA synthesis which is used by the host in that pathway, but acts to inhibit the completion of that pathway (i.e., synthesis of DNA or RNA). More specifically, antimetabolites typically function by (1) competing with metabolites for the catalytic or regulatory site of a key enzyme in DNA or RNA synthesis, or (2) substitute for a metabolite that is normally incorporated into DNA or RNA, and thereby producing a DNA or RNA that cannot support replication. Major categories of antimetabolites include (1) folic acid analogs, which are inhibitors of dihydrofolate reductase (DHFR); and (2) nucleoside analogs including (a) purine analogs, which mimic the natural purines (adenine or guanine) but are structurally different so they competitively or irreversibly inhibit nuclear processing of DNA or RNA; and (b) pyrimidine analogs, which mimic the natural pyrimidines (cytosine, thymidine, and uracil), but are structurally different so they competitively or irreversibly inhibit nuclear processing of DNA or RNA. Non-limiting examples of antimetabolites include: 5-azacytidine; 5-fluoro-2'-deoxycytidine; 5-fluorouracil and 5-fluorouracil prodrugs such as capecitabine and 5-fluorodeoxyuridine monophosphate; cytarabine and cytarabine prodrugs such as nelarabine; 6-azacytidine, adenosine, aminopterin, ancitabine, azacytidine, azathioprine, cladribine, clofarabine, decitabine, elaidicacidcytarabine, erythrohydroxynonyladenine, fazarabine, fludarabine, fluoropyrimidine, forodesine, gemcitabine, mercaptopurine, N4-octadecyl-cytarabine, nelarabine, pentostatin, pseudoisocytidine, thioguanine, troxacitabine and zebularine, derivatives and prodrugs thereof, or their pharmaceutically acceptable salts.

The term "antisense nucleic acid" refers to DNAs or RNAs comprising nucleic acid sequences complementary to the sequence of certain mRNA, or fragments or derivatives thereof, which bind to or hybridize with the complementary sequences in mRNA and inhibit the translation of mRNA into protein.

The term "article of manufacture" broadly encompasses any man-made tangible structural product, for use in the context of the present disclosure.

The terms "co-administering", "co-administration" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "collagen accumulation" refers to the entry of the connective tissue collagen into cells or into the extracellular matrix around cells. This occurs in organs and tissues naturally and under normal circumstances but can occur excessively and accompany or cause disease.

The term "collagen-mediated disorder" refers to a disorder that is characterized by abnormal or undesired collagen accumulation, which when collagen accumulation activity is modified, leads to the desired responses depending on the route of administration and desired end result. A collagen-mediated disorder may be completely or partially mediated through the modulation of collagen accumulation. In particular, a collagen-mediated disorder is one in which modulation of collagen accumulation activity results in some effect on the underlying disorder, e.g., administering a collagen-reducing agent results in some improvement in at least some of the patients being treated. In specific embodiments, the collagen-mediated disorder is a fibroproliferative disorder.

As used herein, the term "combination treatment", which is used interchangeably with the term "combination therapy", refers to situations in which a subject is administered concurrently a combination of two or more therapeutic agents.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined.

As used herein, "delaying progression of a disease" or "decreasing the rate of progression of a disease" means to defer, hinder, slow, retard, stabilize, and/or postpone development of the disease (e.g., a collagen-mediated disorder, including a fibroproliferative disorder such as a fibromatosis). This delay can be of varying lengths of time, depending on the history of the disease and/or individual being treated. As is evident to one skilled in the art, a sufficient or significant delay can, in effect, encompass prevention, in that the individual does not develop the disease. For example, a late stage fibrotic lesion, such as development of a palpable cord, may be delayed.

A "disorder" is any condition that would benefit from treatment including, but not limited to, chronic and acute disorders or diseases including those pathological conditions which predispose a subject to the disorder in question.

An "effective amount" is at least the minimum amount required to effect a measurable improvement or prevention of a particular disease or disorder. An effective amount herein may vary according to factors such as the disease state, age, sex, and weight of the patient, and the ability of a therapeutic agent to elicit a desired response in the individual. An effective amount is also one in which any toxic or detrimental effects of the therapeutic agent are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of a collagen-mediated disorder (e.g., a fibroproliferative disorder such as a fibromatosis), an effective amount includes but is not limited to a shrinkage or reduction in the size of a fibrotic lesion associated with the collagen-mediated disorder (including elimination of the fibrotic lesion), liquefaction, partial liquefaction, or reduction in stiffness (increase in softness) or pressure in or around a fibrotic lesion, a change in viscoelastic properties of the lesion, or reduction in symptoms such as pain, reduction or elimination of flexion contracture or curvature, reduction or elimination of in active or passive extension deficit of joint contracture, and the like. An effective amount can be administered in one or more administrations. For purposes of this disclosure, an effective amount of an agent or, composition is an amount sufficient to accomplish prophylactic or therapeutic treatment either directly or indirectly. As is understood in the clinical context, an effective amount of an agent or composition may or may not be achieved in conjunction with another agent or composition. Thus, an "effective amount" may be considered in the context of administering one or more therapeutic agents, and a single agent may be considered to be given in an effective amount if, in conjunction with one or more other agents, a desirable result may be or is achieved. The therapeutic effect resulting from an effective amount may be objective (i.e., measurable by some test or marker) or subjective (i.e., subject gives an indication of or feels an effect), and may be determined by the clinician or by the patient. Effective amounts will also vary depending on route of administration, as well as the possibility of co-usage with other agents. It will be understood, however, that the total daily usage of the compositions of the present disclosure will be decided by the attending physician within the scope of sound medical judgment. In representative embodiments, an effective amount is one that decreases fibrotic lesion size parameters as follows: (A) Depth: By about 100%, 90%, 80%, 70%, 60%, 50%, 40%, 30%, 25%, or 20%, or 15%, or 10%, or 5%, or 2.5%, or 2%, or 1%; (B) Width: By about 100%, 90%, 80%, 70%, 60%, 50%, 40%, 30%, 25%, or 20%, or 15%, or 10%, or 5%, or 2.5%, or 2%, or 1%; (C) Length: By about 100%, 90%, 80%, 70%, 60%, 50%, 40%, 30%, 25%, or 20%, or 15%, or 10%, or 5%, or 2.5%, or 2%, or 1%; (D) Overall Volume: By about 100%, 90%, 80%, 70%, 60%, 50%, 40%, 30%, 25%, or 20%, or 15%, or 10%, or 5%, or 2.5%, or 2%, or 1%; (E) Surface Area: By about 100%, 90%, 80%, 70%, 60%, 50%, 40%, 30%, 25%, or 20%, or 15%, or 10%, or 5%, or 2.5%, or 2%, or 1%.

As used herein the term "fibroproliferative disorder" or "fibrotic disease or disorder" refers to conditions involving fibrosis in one or more tissues. As used herein the term "fibrosis" refers to the formation of fibrous tissue as a reparative or reactive process, rather than as a normal constituent of an organ or tissue, typically manifesting in a lesion characterized by the activation and proliferation of fibroblasts and increased fibrous connective tissue including collagen deposition in excess of normal deposition. Fibroblasts are connective tissue cells, which are dispersed in connective tissue throughout the body. Fibroblasts secrete a non-rigid extracellular matrix containing type I and/or type III collagen. "Fibrosis" can be used interchangeably with "fibrotic lesion". In specific embodiments, the fibroproliferative disorder is a fibromatosis. The term "fibromatosis" refers to a group of tissues which usually form benign tumors, they are characterized by the absence of cytological and clinical malignancy. It is also distinguished by the proliferation of fibroblasts a growth structure of the type infiltrative and an aggressive clinical behavior with frequent recurrence. Fibromatosis includes diverse subtypes: juvenile fibromatosis, fibromatosis colli, infantile digital fibromatosis, infantile myofibromatosis, ipofibromatosis, fibromatosis hyalinica multiplex, Dupuytren's disease, Peyronie's disease and Ledderhose's disease.

The terms "fibrotic tissue" and "fibrotic lesion" are used interchangeably herein to refer to tissue in which extracellular matrix, mainly collagen, has accumulated in an amount greater than normal. In addition to collagen, examples of the extracellular matrix include, but are not limited to, proteoglycan, tenascin, fibronectin, thrombospondin, osteopontin, osteonectin, and elastin. The amount of collagen accumulated in tissue may be quantified for example by using the amount of hydroxyproline in the tissue as an indicator or by subjecting the tissue to collagen staining (e.g., Masson trichrome staining, Azan staining, sirius red staining, Elastica van Gieson staining, etc.) and carrying out an image analysis. The amount of extracellular matrix in fibrotic tissue in the present disclosure may be at least 5%, at least 10%, at least 25%, at least 50%, at least 100%, at least 200%, at least 300%, at least 400%, or at least 500% compared with that of normal tissue.

The term "fibrosis" refers to the formation of excess fibrous connective tissue as a result of the excess deposition of extracellular matrix components, for example collagen. Fibrous connective tissue is characterized by having extracellular matrix (ECM) with a high collagen content. The collagen may be provided in strands or fibers, which may be arranged irregularly or aligned. The extracellular matrix of fibrous connective tissue may also include glycosaminoglycans.

As used herein, "instructional material" includes a publication, a recording, a diagram, or any other medium of expression which can be used to communicate the usefulness of the compositions and methods of the present disclosure. The instructional material of the kit of the disclosure may, for example, be affixed to a container which contains the therapeutic agents of the disclosure or be shipped together with a container which contains the therapeutic agents disclosed herein.

The term "kit" as used herein refers to a product containing components necessary for carrying out the specified methods (e.g., methods for treating a collagen-mediated disorder including a fibroproliferative disorder such as a fibromatosis, as taught herein), packed so as to allow their transport and storage. Typically, a kit may also include instructions for its use, such as on a package insert including a printed insert or on a computer readable medium.

The term "lesion", as used herein, refers to a tissue abnormality caused by disease or injury. In the context of the present disclosure, the term "lesion" or "fibrotic lesion" is used interchangeably with "fibrotic tissue".

The term "medicament" refers to a drug, and active pharmaceutical ingredient, or the like comprising one or more compounds providing one or more therapeutic or prophylactic benefits to a subject.

A "package insert" is a leaflet that, by order of a Regulatory Authority such as the United States Food and Drug Administration (FDA), must be placed inside the package of every prescription drug. The leaflet generally includes the trademark for the drug, its generic name, and its mechanism of action; states its indications, contraindications, warnings, precautions, adverse effects, and dosage forms; and includes instructions for the recommended dose, time, and route of administration.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Generally, a pharmaceutically acceptable carrier is a non-toxic, inert, solid, semi-solid or liquid filler, diluent, encapsulating material, vehicle, solvent, or formulation auxiliary of any type, and may be made available in individual dosage forms or in bulk. Other dosage forms designed to create a depot of the active compound also are contemplated for use in accordance with the present disclosure. Carriers may include excipients and other additives such as diluents, detergents, coloring agents, wetting or emulsifying agents, pH buffering agents, preservatives, transfection agents and the like. In some embodiments, pharmaceutically acceptable carriers are vehicles capable of suspending and/or dissolving active agents. Carriers may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary carriers include, but are not limited to: butylated hydroxytoluene (BHT), calcium carbonate, calcium phosphate (dibasic), calcium stearate, Croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C and xylitol.

The term "pharmaceutically acceptable salt" as used herein is a broad term, and is to be given its ordinary and customary meaning to a person of ordinary skill in the art (and is not to be limited to a special or customized meaning), and refers without limitation to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17.sup.th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977).

The term "pharmaceutical composition" or "pharmaceutical formulation" refers to a preparation which is in such form as to permit the biological activity of the active ingredient(s) to be effective, and which contains no additional components which are unacceptably toxic to a subject to which the composition or formulation would be administered. Such formulations are typically sterile.

The term "pharmaceutically acceptable carrier" as used herein refers to any carrier, vehicle, excipient, and/or diluent known in the art or otherwise contemplated herein that may improve solubility, deliverability, dispersion, stability, and/or conformational integrity of the compositions disclosed herein.

The term "RNAi molecule" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein or RNA) is down-regulated. Generally, an interfering RNA ("IRNA") is a double stranded short-interfering RNA (SIRNA), short hairpin RNA (shRNA), or single-stranded micro-RNA (miRNA) that results in catalytic degradation of specific mRNAs, and also can be used to lower or inhibit gene expression. The term "short interfering RNA" or "siRNA" (also known as "small interfering RNAs") refers to an RNA agent, preferably a double-stranded agent, of about 10-50 nucleotides in length, preferably between about 15-25 nucleotides in length, more preferably about 17, 18, 19, 20, 21, 22, 23, 24, or 25 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof). The term "miRNA" or "microRNA" refers to an RNA agent, preferably a single-stranded agent, of about 10-50 nucleotides in length, preferably between about 15-25 nucleotides in length, more preferably about 17, 18, 19, 20, 21, 22, 23, 24, or 25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer orthologue or homologue capable of processing dsRNA structures into siRNAs, miRNAs, SIRNA-like or miRNA-like molecules. The term microRNA (or "miRNA") is used interchangeably with the term "small temporal RNA" (or "stRNA") based on the fact that naturally-occurring microRNAs (or "miRNAs") have been found to be expressed in a temporal fashion (e.g., during development). The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

The term "ribozyme" refers to an RNA molecule that has an enzyme-like function, recognizing a particular base sequence and cutting the same. The ribozyme comprises an area that specifically binds to a complementary base sequence of a target messenger RNA strand, and an area that cleaves the target RNA. In certain embodiments, a ribozyme is a Varkud satellite ribozyme, a hairpin ribozyme, a hammerhead ribozyme, or a hepatitis delta ribozyme.

The term "single unit dose" or "single unit dosage form" as used herein means a discrete amount of a pharmaceutical composition comprising a predetermined amount of an active ingredient, or predetermined amounts of two or more active ingredients. The amount of a respective active ingredient is generally equal to the dosage of that active ingredient, which would be administered to a subject, or a convenient part of the dosage, for example, half or third of such dosage. In the context of the present disclosure, a single unit dose generally refers to a discrete amount of a pharmaceutical composition comprising a predetermined amount of a collagen-reducing agent and a hyaluronidase per fibrotic lesion to be treated.

The terms "subject", "patient", "host" or "individual" used interchangeably herein, refer to any subject, particularly a vertebrate subject, and even more particularly a mammalian subject, for whom therapy or prophylaxis is desired. Suitable vertebrate animals that fall within the scope of the disclosure include, but are not restricted to, any member of the subphylum Chordata including primates (e.g., humans, monkeys and apes, and includes species of monkeys such from the genus *Macaca* (e.g., cynomolgus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards etc.), and fish. A preferred subject is a human in need of treatment of a collagen-mediated disorder (e.g., a fibroproliferative disorder such as a fibromatosis). However, it will be understood that the aforementioned terms do not imply that symptoms are present.

As used herein, the term "synergistic" means that the therapeutic effect of a hyaluronidase when administered in combination with a collagen-reducing agent (or vice-versa) or when administered in combination with a collagen-reducing agent and at least one ancillary agent for treating a collagen-mediated disorder (e.g., a fibroproliferative disorder such as a fibromatosis) one or both of a steroid and an antimetabolite ("collagen-reducing agent-ancillary anti-fibrotic agent (CRA-AFA combination"), is greater than the predicted additive therapeutic effects of the hyaluronidase and the collagen-reducing agent, or the hyaluronidase and the CRA-AFA combination, when administered alone. The term "synergistically effective amount" as applied to a hyaluronidase and a collagen-reducing agent or CRA-AFA combination refers to the amount of each component in a composition (generally a pharmaceutical formulation), which is effective for treating a collagen-mediated disorder (e.g., a fibroproliferative disorder such as a fibromatosis), and which produces an effect which does not intersect, in a dose-response plot of the dose of hyaluronidase versus a dose of collagen-reducing agent or CRA-AFA combination versus treatment of the collagen-mediated disorder, either the dose hyaluronidase axis or collagen-reducing agent axis or the CRA-AFA combination axis. The dose response curve used to determine synergy in the art is described for example by Sande et al. (see, p. 1080-1105 in A. Goodman et al., ed., the Pharmacological Basis of Therapeutics, MacMillan Publishing Co., Inc., New York (1980)). The optimum synergistic amounts can be determined, using a 95% confidence limit, by varying factors such as dose level, schedule and response, and using a computer-generated model that generates isobolograms from the dose response curves for various combinations of the hyaluronidase and the collagen-reducing agent or CRA-AFA combination. The highest enhancement in treatment efficacy (e.g., shrinkage or reduction in the size of a fibrotic lesion associated with the collagen-mediated disorder (including elimination of the fibrotic lesion), liquefaction, partial liquefaction, or reduction in stiffness (increase in softness) or pressure in or around a fibrotic lesion, a change in viscoelastic properties of the lesion, or reduction in symptoms such as pain, reduction or elimination of flexion contracture or curvature, reduction or elimination of in active or passive extension deficit of joint contracture, and the like) on the dose response curve correlates with the optimum dosage levels.

As used herein, the term "treatment" refers to clinical intervention designed to alter the natural course of the individual being treated during the course of clinical pathology. Desirable effects of treatment include decreasing the rate of disease progression, ameliorating or palliating the disease state, and remission or improved prognosis. For example, an individual is successfully "treated" if one or more symptoms associated with a collagen-mediated disorder (e.g., fibroproliferative disorder) are mitigated or eliminated, including, but are not limited to, a shrinkage or reduction in the size of a fibrotic lesion associated with the collagen-mediated disorder (including elimination of the fibrotic lesion), liquefaction, partial liquefaction, or reduction in stiffness (increase in softness) or pressure in or around a fibrotic lesion, a change in viscoelastic properties of the lesion, or reduction in symptoms such as pain, reduction or elimination of flexion contracture or curvature, reduction or elimination of in active or passive extension deficit of joint contracture, and the like.

As used herein, the term "treatment efficacy", "efficacy" and variants thereof are generally indicated by alleviation of one or more signs or symptoms associated with a disease and can be readily determined by one skilled in the art. "Treatment efficacy" may also refer to the prevention or amelioration of signs and symptoms of toxicities typically associated with standard or non-standard treatments of a disease.

Determination of treatment efficacy is usually indication and disease specific and can include any methods known or available in the art for determining that a treatment is providing a beneficial effect to a subject. For example, evidence of treatment efficacy can include but is not limited to general improvements in the overall health of the subject, such as but not limited to enhancement of patient life quality, increase in predicted subject survival rate, decrease in depression, decreasing the severity and/or frequency one or more symptoms resulting from the disease, diminishing the extent of the disease, stabilizing the disease (e.g., preventing or delaying the worsening of the disease), delay or slowing the progression of the disease, ameliorating the disease state, etc. In some embodiments of the disclosure, the treatment efficacy is clinical efficacy or is statistically significant.

As used herein, the term "Unit (U)" refers to "International Unit (IU)". The term "International Unit" refers to an internationally accepted amount of a biologically active substance required to produce a specific response. All international units are officially defined by the International Conference for Unification of Formulae. The term "International Unit" can be abbreviated as "IU" or "U" in English, UI in French and Italian, and IE in German. Weight equivalents to International Units of enzymes disclosed herein are known in the art and can be determined using standard assays.

The terms "vector" and "expression vector" refer to a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators).

A "vial" is a container suitable for holding a liquid or lyophilized preparation. In some embodiments, the vial is a single-use vial, e.g., a 10 mL or a 20 mL single-use vial, optionally with a stopper, including for example a 10 mL single use glass vial with a 20 mm stopper.

Each embodiment described herein is contemplated as being applicable to each of the other disclosed embodiments. In addition, the elements recited in the packaging and pharmaceutical composition embodiments can be used in the method and use embodiments described herein.

2. Compositions and Methods for Treatment of Fibroses

The compositions and methods of the present disclosure enable treatment, prevention, inhibition of progression and/or reversal of conditions associated with excessive or uncontrolled production of extracellular matrix, especially ones associated with fibrosis and/or collagen deposition. In particular, the present disclosure enables improved treatment of collagen-mediated disorders such as fibroproliferative disorders, representative examples of which include hypertrophic scar, hyperplastic scar, keloid scar, liver fibrosis, lung fibrosis, skin fibrosis, muscle fibrosis, kidney fibrosis, glomerulosclerosis, uterine fibrosis, radiation fibrosis, and fibromatoses, including for example fascial fibromatoses such as adhesive capsulitis, Dupuytren's disease, Peyronie's disease and Ledderhose's disease.

The methods and compositions disclosed herein are based in large part on the determination that hyaluronidase markedly improves the treatment of a collagen-mediated disorder (e.g., fibroproliferative disorder such as a fibromatosis) by a collagen-reducing agent, including significantly reducing the mean time required to reduce the size or volume of a fibrotic tissue, shrink a fibrotic tissue, degrade a fibrotic tissue, change the viscoelastic properties of a fibrotic tissue, soften a fibrotic tissue, relax a fibrotic tissue, stretch a fibrotic tissue, or eliminate at least a portion of a fibrotic tissue associated with the collagen-mediated disorder. Without wishing to be bound to theory or mode of operation, it is believed that hyaluronidase depolymerizes or otherwise degrades hyaluronan (HA) in the extracellular matrix of a fibrotic lesion, which changes the viscoelastic properties of the lesion to facilitate increased hydraulic conductance of a co-administered collagen-reducing agent, thereby markedly improving its penetration into the extracellular matrix of the lesion.

Hyaluronidases belong to a family of hydrolase enzymes that degrade glycosaminoglycans (GAG). Mammalian hyaluronidases catalyze hydrolysis of β-1-4 linkages between N-acetyl-β-D-glucosamine and D-glucoronate residues in hyaluronate, chondroitin, chondroitin 4- and 6-sulfates, and dermatan. HA is a non-sulfated GAG and an important viscoelastic constituent of the interstitial matrix that forms part of the connective tissue, skin, cartilage and synovial fluid. This megadalton disaccharide composed of N-acetylglucosamine and glucuronic acid repeats is produced by fibroblasts and secreted into the hypodermal interstitium; its degradation occurs mainly in the lymph nodes, liver, and in-situ by way of lysosomal hyaluronidases and exoglycosidases.

Functionally, animal-derived hyaluronidases (e.g., sheep, bovine, bee) are catalytically active without N-glycan moieties, as opposed to recombinant human hyaluronidases, which require at least one N-glycosylation site as well as disulfide bonds for activity.

In some embodiments, the hyaluronidase is mammalian, representative classes of which include:
1. Mammalian-type hyaluronidases, (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates (CS), generally C4-S and C6-S.
2. Bacterial hyaluronidases (EC 4.2.99.1) degrade hyaluronan and, and to various extents, CS and DS. They are endo-beta-N-acetylhexosaminidases that operate by a beta elimination reaction that yields primarily disaccharide end products.
3. Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: neutral-active and acid-active enzymes. There are six hyaluronidase-like genes in the human genome, HYAL1, HYAL2, HYAL3, HYAL4, HYALP1 and PH20/SPAM1. HYALP1 is a pseudogene, and HYAL3 has not been shown to possess enzyme activity toward any known substrates. HYAL4 is a chondroitinase and exhibits little activity towards hyaluronan. HYAL1 is the prototypical acid-active enzyme and PH20 is the prototypical neutral-active enzyme. Acid-active hyaluronidases, such as HYAL1 and HYAL2 generally lack catalytic activity at neutral pH (i.e. pH 7). For example, HYAL1 has little catalytic activity in vitro over pH 4.5 (Frost I. G. and Stern, R., "A microtiter-based assay for hyaluronidase activity not requiring specialized reagents", Anal. Biochemistry, 1997; 251:263-269). HYAL2 is an acid-active enzyme with a very low specific activity in vitro.

The hyaluronidase-like enzymes can also be characterized by those which are generally locked to the plasma membrane via a glycosylphosphatidyl inositol anchor such as human HYAL2 and human PH20 (Danilkovitch-Miagkova et al., *Proc. Natl. Acad. Sci. USA*, 2003; 100(8): 4580-4585; Phelps et al., Science 1988; 240(4860): 1780-1782), and those which are generally soluble such as human HYAL1 (Frost, I. G. et al., "Purification, cloning, and expression of human plasma hyaluronidase", *Biochem. Biophys. Res. Commun.* 1997; 236(1): 10-15). However, there are variations from species to species: bovine PH20 for example is very loosely attached to the plasma membrane and is not anchored via a phospholipase sensitive anchor (Lalancette et al., *Biol Reprod.*, 2001; 65(2):628-36). This unique feature of bovine hyaluronidase has permitted the use of the soluble bovine or ovine testes hyaluronidase enzyme as an extract for clinical use (WYDASE, HYALASE).

In some embodiments, the hyaluronidase for use in the compositions disclosed herein is recombinant and is obtained from a mammalian, microbial, or plant expression system. In some embodiments, the hyaluronidase is mammalian. In some embodiments, the hyaluronidase comprises the sequence set forth in NCBI Accession No. NP_001167515.1 (GI: 291290979) (GI: 291290979). In some embodiments, the hyaluronidase is a functional fragment of the sequence set forth in NCBI Accession No. NP_001167515.1 (GI: 291290979). In some embodiments, the hyaluronidase is a truncated form of the sequence set forth in NCBI Accession No. NP_001167515 (GI: 291290979). In specific embodiments, the hyaluronidase is animal-derived. In some embodiments, the hyaluronidase is a sheep or bovine hyaluronidase. In illustrative examples of this type, the hyaluronidase comprises the sequence set forth in NCBI Accession No. XP_042104697.1 (GI: 2062893006) or AAP55713.1 (GI: 31616581). In some embodiments, the animal-derived hyaluronidase is rHuPH20/HYLENEX, AMPHADASE, HYALASE, HYDASE, HYLASE, VITRASE OR WYDASE. In further embodiments, the hyaluronidase is in modified form. The minimum purity or specific activity of the hyaluronidase component used in the composition is generally at least 1,000 U/mg United States Pharmacopeia (USP), suitably at least 1,500 U/mg USP. In specific embodiments, the hyaluronidase is HYALASE.

The collagen-reducing agent includes any substance that can reduce the amount of collagen accumulated in tissue. For example, the collagen-reducing agent may be selected from a collagen degradation agent, a suppressor of collagen production by collagen-producing cells, and a suppressor of a collagen degradation inhibitor. Although there is no particular limitation, the collagen in the present disclosure is suitably a collagen involved in fibrosis such as for example type I, III, or V collagen, and particularly preferably type I collagen, which is present in fibrotic tissue in the largest amount.

Exemplary collagen degradation agents include, but are not limited to, collagenase and collagenase producing substances. Non-limiting examples of collagenases include bacterial collagenases or mammalian matrix metalloproteinases (also referred to herein as "mammalian collagenases"). Examples of bacterial collagenase include clostridial collagenases, suitably a clostridial type II collagenases (e.g., a type II collagenase from *Clostridium histolyticum* such as Collagenase G or Collagenase H). Representative mammalian matrix metalloproteinases include for example human matrix metalloproteinase such as human metalloproteinase-1 (MMP-1), human metalloproteinase-2 (MMP-2), human metalloproteinase-3 (MMP-3), human metalloproteinase-7 (MMP-7), human metalloproteinase-8 (MMP-8), human metalloproteinase-9 (MMP-9), human metalloproteinase-10 (MMP-10), human metalloproteinase-11 (MMP-11), metalloproteinase-12 (MMP-12), human metalloproteinase-13 (MMP-13) and human metalloproteinase-13 (MMP-14).

In some embodiments, the collagen-reducing agent is a collagenase-producing agent, which promotes endogenous production of collagenase (also referred to herein as an "endogenous collagenase production-stimulating agent"). Representative collagenase-producing agents include, but are not limited to, plasminogen and components of the plasminogen-activating pathway or have the capacity to activate plasminogen directly or via the plasminogen-activating pathway, representative examples of which include tissue plasminogen activator (tPA), urokinase type plasminogen activator (uPA), kallikrein, Factor XII, streptokinase, saruplase, alteplase, reteplase, tenecteplase, anistreplase, monteplase, lanoteplase, parniteplase, staphylokinase and recombinant forms and variants of plasminogen and components of the plasminogen-activating pathway. The collagenase-producing agents may be animal derived or recombinant. Thus, in some embodiments, the collagenase-producing agent is recombinant, and in representative embodiments of this type, the collagenase-producing agent is recombinant and is obtained from a mammalian, microbial, or plant expression system. In some embodiments, the collagenase-producing agent is human. In non-limiting examples of this type, the collagenase-producing agent is a plasminogen activator selected from a tPA comprising the sequence set forth in any one of NCBI Accession No. NP_001306118.1 (GI: 984290524), NP_127509.1 (GI 14702169) and NP_000921.1 (GI: 4505861), or a uPA comprising the sequence set forth in any one of NP_002649.2 (GI: 1788951006), NP_001138503.2 (GI: 1788951003) and NP_001306120.2 (GI: 1788951008). In further embodiments, the plasminogen activator is in modified form. The minimum purity or specific activity of the plasminogen activator component used in the composition is generally at least 400,000 U/mg United States Pharmacopeia (USP), suitably at least 500,000 U/mg USP, and is typically in the range of 522,000 to 696,000 U/mg. In certain embodiments, the collagenase-producing agent is alteplase (ACTILYSE).

Alternatively, the collagen-reducing agent is a suppressor of collagen production by collagen-producing cells. Collagen-producing cells encompass any cells that produce collagen in fibrotic tissue, illustrative examples of which include activated stellate cells and myofibroblasts.

The suppressor of collagen production by collagen-producing cells includes any agent that directly or indirectly suppresses the physical, chemical, and/or physiological actions, etc. of same cells involved in collagen accumulation in fibrotic tissue, and examples thereof include, but are not limited to, a TGFβ (Transforming growth factor-beta) inhibitor, HGF (Hepatocyte growth factor) or a substance promoting the production thereof, a PPARγ (Peroxisome proliferator-activated receptor gamma) ligand, an angiotensin inhibitor, a PDGF (Platelet-derived growth factor) inhibitor, relaxin or a substance promoting the production thereof, a substance that inhibits the production and secretion of an extracellular matrix component, a cell activity suppressor, and an apoptosis-inducing substance.

Examples of TGFβ inhibitors include, but are not limited to, a truncated TGFβ type II receptor (Qi et al., *Proc Natl Acad Sci USA*. 1999; 96 (5): 2345-9), a soluble TGFβ type II receptor (George et al., *Proc Natl Acad Sci USA*. 1999; 96 (22): 12719-24), a TGFβ activity inhibitor such as an anti-TGFβ antibody, a TGFβ production inhibitor such as an RNAi molecule, ribozyme, or antisense nucleic acid complementary to TGFβ, vectors expressing these, and cells transformed thereby.

Non-limiting examples of substances promoting the production of HGF or relaxin include a nucleic acid coding for HGF or relaxin, an expression construct containing this, expression vectors containing these, and cells transformed thereby.

Representative examples of the PPARγ ligands include, but are not limited to, an endogenous ligand such as 15-deoxy-δ12,14-prostaglandin J2, nitrolinoleic acid, oxidized LDL (Low density lipoprotein), a long chain fatty acid, or an eicosanoid, and an exogenous ligand such as a thiazolidinedione medicinal agent such as troglitazone, pioglitazone, rosiglitazone, balaglitazone or rivoglitazone, or a non-steroidal anti-inflammatory drug.

Examples of angiotensin inhibitors include, but are not limited to, an angiotensin receptor antagonist such as telmisartan, losartan, valsartan, candesartan cilexetil, olmesartan medoxomil, or irbesartan. The angiotensin includes angiotensins I, II, III, and IV. Furthermore, examples of the angiotensin receptor include, but are not limited to, an angiotensin type 1 receptor (AT1).

Illustrative examples of PDGF inhibitors include a PDGF activity inhibitor such as an anti-PDGF antibody, a PDGF production inhibitor such as an RNAi molecule, ribozyme, or antisense nucleic acid complementary to PDGF, vectors expressing these, and cells transformed thereby.

Examples of the substance that inhibits the production and secretion of an extracellular matrix component include, but are not limited to, a substance such as an RNAi molecule, a ribozyme, or an antisense nucleic acid, which suppresses the expression of an extracellular matrix component such as collagen, proteoglycan, tenascin, fibronectin, thrombospondin, osteopontin, osteonectin, or elastin, a substance having a dominant negative effect such as a dominant negative mutant, vectors expressing these, and cells transformed thereby. Representative examples of substances that inhibit the production and secretion of collagen include, but are not limited to, inhibitors of HSP (Heat shock protein) 47, which is a collagen-specific molecular chaperone essential for intracellular transport and molecular maturation common to the synthetic processes for various types of collagen, for example HSP47 expression inhibitors such as an RNAi molecule, ribozyme, or antisense nucleic acid complementary to HSP47, a substance having a dominant negative effect such as an HSP47 dominant negative mutant, vectors expressing these, and cells transformed thereby. Examples of the cell activity suppressors include, but are not limited to, a sodium channel inhibitor. Non-limiting examples of apoptosis-inducing agents include compound 861, gliotoxin, and atorvastatin.

In other embodiments, the collagen-reducing agent is a suppressor of a collagen degradation inhibitor such as, but not limited to, TIMP (tissue inhibitor of metalloproteinase, TIMP1 and TIMP2, etc.). Therefore, examples of the suppressor of the above inhibitor include, but are not limited to, a TIMP activity inhibitor such as an antibody for TIMP, a TIMP production inhibitor such as an RNAi molecule, ribozyme, or antisense nucleic acid complementary to TIMP, vectors expressing these, and cells transformed thereby.

In preferred embodiments, the compositions of the present disclosure comprise, consist or consist essentially of a hyaluronidase and a collagenase-producing agent.

In representative embodiments of this type, the hyaluronidase is present in the composition at a concentration of about 1 U/mL to about $2\times10^3$ U/mL (and all integer concentrations in between), about 10 U/mL to about $1\times10^3$ U/mL (and all integer concentrations in between), about 40 U/mL to about $5\times10^2$ U/mL (and all integer concentrations in between), about 60 U/mL to about $4\times10^2$ U/mL (and all integer concentrations in between), about 80 U/ml to about $3\times10^2$ U/mL (and all integer concentrations in between), about $1\times10^2$ U/mL to about $2\times10^2$ U/mL (and all integer concentrations in between), or about $1.2\times10^2$ U/mL to about $1.8\times10^2$ U/mL (and all integer concentrations in between).

In related embodiments, the hyaluronidase is in an amount corresponding to about 10 U to about $2\times10^4$ U (and all integer units in between), about $1\times10^2$ U to about $1\times10^4$ U (and all integer units in between), about $4\times10^2$ U to about $5\times10^3$ U (and all integer units in between), about $6\times10^2$ U to about $4\times10^3$ U (and all integer units in between), about $8\times10^2$ U to about $3\times10^3$ U (and all integer units in between), about $1\times10^3$ U to about $2\times10^3$ U (and all integer units in between), or about $1.2\times10^3$ U to about $1.8\times10^3$ U (and all integer units in between) per single unit dose.

In other related embodiments, the hyaluronidase is in an amount of about 0.01 mg to about 20 mg (and all one-hundredth milligram units in between), about 0.05 mg to about 10 mg (and all one-hundredth milligram units in between), about 0.1 mg to about 5 mg (and all one-tenth milligram units in between), about 0.2 mg to about 4 mg (and all one-tenth milligram units in between), about 0.3 mg to about 3 mg (and all one-tenth milligram units in between), or about 0.4 mg to about 2 mg (and all one-tenth milligram units in between) per single unit dose.

In some embodiments, the collagenase-producing agent is a plasminogen activator such as tissue plasminogen activator (tPA) or a urokinase type plasminogen activator (uPA). The plasminogen activator may be present in the composition at a concentration of about $1\times10^4$ U/mL to about $1\times10^7$ U/mL (and all integer concentrations in between), about $5\times10^4$ U/ml to about $5\times10^6$ U/mL (and all integer concentrations in between), about $1\times10^5$ U/mL to about $4\times10^6$ U/mL (and all integer concentrations in between), about $2\times10^5$ U/mL to about $3\times10^6$ U/mL (and all integer concentrations in between), about $3\times10^5$ U/mL to about $2\times10^6$ U/mL (and all integer concentrations in between), or about $4\times10^5$ U/mL to about $1\times10^6$ U/mL (and all integer concentrations in between).

In related embodiments, the plasminogen activator is in an amount corresponding to about $1\times10^5$ U to about $1\times10^8$ U (and all integer units in between), about $5\times10^5$ U to about $5\times10^7$ U (and all integer units in between), about $1\times10^6$ U to about $4\times10^7$ U (and all integer units in between), about $2\times10^6$ U to about $3\times10^7$ U (and all integer units in between), about $3\times10^6$ U to about $2\times10^7$ U (and all integer units in between), about $4\times10^6$ U to about $1\times10^7$ U (and all integer units in between) per single unit dose.

In other related embodiments, the plasminogen activator is in an amount of about 0.1 mg to about 200 mg (and all one-tenth milligram units in between), about 0.5 mg to about 100 mg (and all one-tenth milligram units in between), about 1 mg to about 50 mg (and all one-tenth milligram units in between), about 2 mg to about 40 mg (and all one-tenth milligram units in between), about 3 mg to about 30 mg (and all one-tenth milligram units in between), about 4 mg to about 20 mg (and all one-tenth milligram units in between) per single unit dose.

Suitably, the molar ratio of plasminogen activator to hyaluronidase in the composition is from about 50:1 to 5:1 (and all integer ratios in between), about 40:1 to 5:1 (and all integer ratios in between), about 30:1 to 5:1 (and all integer ratios in between), about 20:1 to 5:1 (and all integer ratios in between), 50:1 to 10:1 (and all integer ratios in between), about 40:1 to 10:1 (and all integer ratios in between), about 30:1 to 10:1 (and all integer ratios in between), or about 20:1 to 10:1 (and all integer ratios in between).

The compositions disclosed herein may further comprise at least one ancillary anti-fibrotic agent, which is suitably selected from a steroid and an antimetabolite.

The steroid is typically a corticosteroid, representative examples of which include betamethasone, betamethasone acetate, betamethasone sodium phosphate, loteprednol, triamcinolone, triamcinolone acetonide, triamcinolone diacetate, triamcinolone benetonide, triamcinolone furetonide, triamcinolone hexacetonide, dexamethasone, fluorometholone, fluocinolone acetonide, prednisone, prednisolone, methylprednisone, corticol, cortisone, fluorocortisone, deoxycorticosterone acetate, aldosterone, and budesonide, their derivatives, prodrugs and pharmaceutically acceptable salts, and combinations thereof. In certain embodiments, the steroid is triamcinolone, a triamcinolone derivative, a triamcinolone prodrug or a pharmaceutically acceptable salt thereof.

The corticosteroid (e.g., triamcinolone, a triamcinolone derivative, a triamcinolone prodrug or a pharmaceutically acceptable salt thereof) may be present in the composition at a concentration of about 0.1 mg/mL to about 60 mg/ml (and all one-tenth unit concentrations in between), about 0.2 mg/mL to about 50 mg/ml (and all one-tenth unit concentrations in between), about 0.4 mg/mL to about 40 mg/mL (and all one-tenth unit concentrations in between), about 0.6 mg/mL to about 30 mg/ml (and all one-tenth unit concentrations in between), about 0.8 mg/mL to about 20 mg/ml (and all one-tenth unit concentrations in between), or about 1 mg/mL to about 10 mg/ml (and all one-tenth unit concentrations in between).

In specific embodiments, the corticosteroid (e.g., triamcinolone, a triamcinolone derivative, a triamcinolone prodrug or a pharmaceutically acceptable salt thereof) may be present in the composition in an amount of about 1 mg to about 600 mg (and all integer milligram units in between), 2 mg to about 500 mg (and all integer milligram units in between), about 4 mg to about 400 mg (and all integer milligram units in between), about 6 mg to about 300 mg (and all integer milligram units in between), about 8 mg to about 200 mg (and all integer milligram units in between), about 10 mg to about 100 mg (and all integer milligram units in between), or about 12 mg to about 80 mg (and all integer milligram units in between) per single unit dose.

In some embodiments, the molar ratio of hyaluronidase to corticosteroid (e.g., triamcinolone, a triamcinolone derivative, a triamcinolone prodrug or a pharmaceutically acceptable salt thereof) in the composition is from about 1:100000 to 1:10000 (and all integer ratios in between), about 1:80000 to 1:10000 (and all integer ratios in between), about 1:60000 to 1:10000 (and all integer ratios in between), about 1:40000 to 1:10000 (and all integer ratios in between), 1:100000 to 1:20000 (and all integer ratios in between), about 1:80000 to 1:20000 (and all integer ratios in between), about 1:60000 to 1:20000 (and all integer ratios in between), about 1:40000 to 1:20000 (and all integer ratios in between), about 1:50000 to 1:5000 (and all integer ratios in between), about 1:40000 to 1:5000 (and all integer ratios in between), about 1:30000 to 1:5000 (and all integer ratios in between), about 1:20000 to 1:5000 (and all integer ratios in between), 1:50000 to 1:10000 (and all integer ratios in between), about 1:40000 to 1:10000 (and all integer ratios in between), about 1:30000 to 1:10000 (and all integer ratios in between), or about 1:20000 to 1:10000 (and all integer ratios in between).

The antimetabolite may be selected from 5-azacytidine; 5-fluoro-2'-deoxycytidine; 5-fluorouracil and 5-fluorouracil prodrugs such as capecitabine and 5-fluorodeoxyuridine monophosphate; cytarabine and cytarabine prodrugs such as nelarabine; 6-azacytidine, adenosine, aminopterin, ancitabine, azacytidine, azathioprine, cladribine, clofarabine, decitabine, elaidicacidcytarabine, erythrohydroxynonyladenine, fazarabine, fludarabine, fluoropyrimidine, forodesine, gemcitabine, mercaptopurine, N4-octadecyl-cytarabine, nelarabine, pentostatin, pseudoisocytidine, thioguanine, troxacitabine and zebularine, derivatives and prodrugs thereof, or their pharmaceutically acceptable salts. In certain embodiments, the antimetabolite is 5-fluorouracil, a 5-fluorouracil derivative, a 5-fluorouracil prodrug, or a pharmaceutically acceptable salt thereof.

The antimetabolite (e.g., 5-fluorouracil, a 5-fluorouracil derivative, a 5-fluorouracil prodrug, or a pharmaceutically acceptable salt thereof) may be present in the composition at a concentration of about 0.01 mg/mL to about 5 mg/ml (and all integer concentrations in between), about 0.02 mg/mL to about 4 mg/ml (and all integer concentrations in between), about 0.04 mg/mL to about 3 mg/mL (and all integer concentrations in between), about 0.06 mg/mL to about 2 mg/ml (and all integer concentrations in between), about 0.08 mg/mL to about 1.6 mg/ml (and all integer concentrations in between), about 0.1 mg/ml to about 1.2 mg/mL (and all integer concentrations in between), or about 0.2 mg/ml to about 1 mg/ml (and all integer concentrations in between).

In some embodiments, the antimetabolite (e.g., 5-fluorouracil, a 5-fluorouracil derivative, a 5-fluorouracil prodrug, or a pharmaceutically acceptable salt thereof) may be present in the composition in an amount of about 0.1 mg to about 50 mg (and all one-tenth milligram units in between), about 0.2 mg to about 40 mg (and all one-tenth milligram units in between), about 0.4 mg to about 30 mg (and all one-tenth milligram units in between), about 0.6 mg to about 20 mg (and all one-tenth milligram units in between), about 0.8 mg to about 16 mg (and all one-tenth milligram units in between), about 1 mg to about 12 mg (and all one-tenth milligram units in between), or about 2 mg to about 10 mg (and all one-tenth milligram units in between) per single unit dose.

In some embodiments, the molar ratio of hyaluronidase to antimetabolite (e.g., 5-fluorouracil, a 5-fluorouracil derivative, a 5-fluorouracil prodrug, or a pharmaceutically acceptable salt thereof) in the composition is from about 1:10000 to 1:1000 (and all integer ratios in between), about 1:8000 to 1:1000 (and all integer ratios in between), about 1:6000 to 1:1000 (and all integer ratios in between), about 1:4000 to 1:1000 (and all integer ratios in between), 1:10000 to 1:2000 (and all integer ratios in between), about 1:8000 to 1:2000 (and all integer ratios in between), about 1:6000 to 1:2000 (and all integer ratios in between), about 1:4000 to 1:2000 (and all integer ratios in between), about 1:5000 to 1:500 (and all integer ratios in between), about 1:4000 to 1:500 (and all integer ratios in between), about 1:3000 to 1:500 (and all integer ratios in between), about 1:2000 to 1:500 (and all integer ratios in between), 1:5000 to 1:1000 (and all integer ratios in between), about 1:4000 to 1:1000 (and all integer ratios in between), about 1:3000 to 1:1000 (and all integer ratios in between), or about 1:2000 to 1:1000 (and all integer ratios in between).

The compositions may further comprise a buffering agent suitable to adjust the pH of the composition to a pH of about 5 to 8. Generally, the buffering agent provides a pH of about 5 to 8, and in specific embodiments is selected from 5.5, 5.6, 5.7, 5.8, 5.9, 60, 6.1, 6.2, 6.3, 6.4, 6.5, 6.6, 6.7, 6.8, 6.9, 7.0, 7.1, 7.2, 7.3, 7.4, 7.5 and 7.6. In representative examples of this type, the buffering agent is suitable to adjust the pH of the composition to one approximating physiological blood.

The buffering agent is suitably an alkaline buffering agent, representative examples of which include amino acids, alkaline metal salts of amino acids, aluminum hydroxide, aluminum hydroxide/magnesium carbonate/calcium carbonate co-precipitate, aluminum magnesium hydroxide, aluminum hydroxide/magnesium hydroxide co-precipitate, aluminum hydroxide/sodium bicarbonate coprecipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tefrasodium pyrophosphate, tripotassium phosphate, trisodium phosphate, and frometamol. In certain embodiments, the alkaline buffering agent is selected from bicarbonates, including for example sodium bicarbonate, magnesium bicarbonate and calcium bicarbonate.

The compositions may optionally further comprise a substance that reduces a fibrotic stimulus as an active ingredient, or may be used in combination with such a substance. Examples of the substance that reduces a fibrotic stimulus include, but are not limited to, an antioxidant, a blood circulation promoter, an anti-inflammatory drug, an antiviral drug, an antibiotic, an antiparasitic agent, a liver protection drug, a choleretic drug, and an apoptosis suppressor. These substances may be selected as appropriate according to the tissue that is targeted and the disease state.

The compositions disclosed herein may include a pharmaceutically acceptable carrier. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

The pharmaceutical compositions disclosed herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

In representative examples of this type, the compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington: The Science and Practice of Pharmacy, supra).

In some embodiments, the compositions intended for parenteral administration can include one or more pharmaceutically acceptable carriers, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In illustrative examples, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Representative antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL, CyDex, Lenexa, Kans.).

In specific embodiments, the compositions of the present disclosure are administered by injection, insertion or implantation directly into or onto or adjacent to the fibrotic tissue to be treated, i.e., local administration to the tissue to be treated. Other modes of administration contemplated included, but are not limited to instillation or application onto the affected tissues, instillation or application during surgery (such as fasciotomy) onto the affected tissues, i.e., topical administration to the fibrotic tissue, by spray or other application of a liquid, fluid or gel formulation.

Suitably, when the pharmaceutical compositions provided herein are formulated for parenteral administration, they typically contain an antimicrobial agent at bacteriostatic and/or fungistatic concentrations. All parenteral formulations are generally sterile, as known and practiced in the art.

The compositions for parenteral administration may be provided as ready-to-use sterile solutions. Alternatively, the compositions may be provided as sterile dry soluble products, including lyophilized powders and hypodermic tablets, to be reconstituted with a vehicle prior to use. In other embodiments, the compositions are provided as ready-to-use sterile suspensions. In still other embodiments, the compositions are provided as sterile dry insoluble products to be reconstituted with a vehicle prior to use. In further embodiments, the compositions are provided as ready-to-use sterile emulsions.

In specific embodiments, the hyaluronidase and collagen-reducing agent are administered locally, e.g., by applying directly into a surgical incision during surgery, by injection, preferably directly into the fibrotic lesion (e.g., clinical nodule(s) and/or cord tissue), by release from a sustained and/or delayed release dosage form or device that may be implanted into or close to the disease site or a sustained and/or delayed release patch formulation, by topical application or any other suitable route.

The compositions disclosed herein may be locally administered to fibrotic tissue in a variety of forms, by a variety of routes, using a variety of apparatuses. In some embodiments, the formulation is injected/inserted using an apparatus consisting of a simple needle (e.g., having a size in the range of about 18 gauge to about 27 gauge, and suitably about 20 gauge to about 27 gauge) and sample pusher. For example, according to one embodiment, a composition of the present disclosure is placed in the needle or in a syringe or other chamber affixed to the needle. Once the needle is placed at the desired depth and location in the tissue, the pusher is used to push the sample from the needle and into the tissue.

In still other embodiments, compositions in accordance with the present disclosure are injected/inserted via jet injection without a physical delivery channel such as a needle, as is known in the art. Typically, a compression system (e.g., a mechanical system or a gas, such as helium, nitrogen, carbon dioxide, etc.) is used to accelerate the composition to a high enough velocity so that the composition can penetrate the tissue to a desired depth. Jet injector devices can be, for example, disposable, or reusable with medication cartridges that are prefilled or non-prefilled medication cartridges. Examples of jet injectors include Biojector from Bioject, N.J., USA and the PowderJect™ System from PowderJect, UK. In other embodiments, a device is employed that cores out a section of the fibrotic tissue (e.g., a biopsy device or tissue morcellator or laser radiation), thereby leaving behind a void for insertion of a dosage form.

The compositions of the present disclosure are generally contemplated to comprise injectable or implantable formulations, or any fluid, liquid, solid, semi-solid, gel, or other composition which is suitable to administer the hyaluronidase and collagen-reducing agent, and optionally other agents disclosed herein to the fibrotic tissue to be treated. Compositions in accordance with the present disclosure may be formulated by any method known in the pharmaceutical arts. Thus, any injectable or implantable formulation known in the art and consistent with hyaluronidase activity and collagen-reducing agent activity may be used. Compositions which create a depot or extended release of the active hyaluronidase and collagen-reducing agent are contemplated. For example, injectable extended or sustained release compositions are contemplated, however any implantable formulation can be used. Such compositions produce or form a depot effect, where active agent is present in the tissue where administered and release active agent over a period of time to continuously treat the tissue. In specific embodiments, the present disclosure provides immediate release injectable compositions, where the active agents are immediately released for activity upon administration.

In some embodiments, the injectable or insertable compositions of the present disclosure are solids, semi-solids or high-viscosity fluids. This may improve dosage retention in the tissue, thereby improving delivery efficiency of the treatment agents and/or minimizing the adverse effects such as unintended, nonspecific tissue damage. "High viscosity" and other such terms are used herein to describe fluids having viscosities greater than 1000 centipoise as measured by any of a number of standard techniques, including, for example, a Brookfield Kinematic Viscometer, model HBDV-II+CP with a CPE-40 cone spindle, set at 37.degree. C. and using a 0.5 rpm speed setting. "Low viscosity" fluids have viscosities less than this value.

In some embodiments, a composition of the present disclosure is injected into a patient in a fluid state, whereupon it converts (or is converted) in vivo into a more readily retained form, for example, into a solid form (including conversion of an injected liquid into a solid, conversion of an injected semi-solid into a solid and conversion of a liquid into a gel), into a semi-solid form (including conversion of an injected liquid into a semi-solid, conversion of an injected semi-solid into a semi-solid having increased yield stress and/or viscosity and conversion of a liquid into a gel), or into a high-viscosity fluid (including conversion of a low-viscosity fluid into a high-viscosity fluid, and conversion of a high-viscosity fluid into a higher-viscosity fluid). Exemplary formulations of this type may include a carrier or nanocarrier. Appropriate carriers include solid or semi-solid pellets, beads or gel-forming polymers, high-viscosity liquids and the like to maintain the active hyaluronidase and collagen-reducing agent in the tissue, protecting the active enzymes (e.g., hyaluronidase and collagen-reducing agent such as plasminogen activator, collagenase and the like) from action of the tissue or tissue components which could inactivate these agents, and allow steady release of the agents to the tissue for treatment. Any injectable dosage form which can protect and contain the active agents(s) in place may be used.

Other dosage forms designed to create a depot of the active agents are also contemplated herein. Dosage forms for hyaluronidase and collagen-reducing agent suitable for use in accordance with the present disclosure include, but are not limited to lyophilized or other dried powder for reconstitution prior to injection, in multiple or single dose amounts, individual dosage units ready for injection (which suitably also include one or more preservatives), frozen unit dosage forms, or any mode of preparation known in the art.

The compositions described herein are preferably injected into one or more individual fibrotic tissues using a hollow delivery channel, such as a hollow needle or cannula. For instance, administration can be performed using a needle in association with a conventional or specially designed syringe, cannula, catheter, and the like. A source of manual, mechanical, hydraulic, pneumatic or other means to apply pressure (e.g., a conventional syringe plunger, a pump, aerosol, etc.) can be used to inject the composition into the fibrotic tissue. Alternatively, the formulations can be administered during surgery (e.g., fasciotomy).

Where the compositions have fluid attributes, the injection volume will vary, depending, for example, on the size of the fibrotic tissue, the type and concentration of treatment agent, and so forth, and will typically range from 1.0 to 25 mL per injection. In illustrative examples of this type, the compositions are in a single unit dosage form (e.g., single-use vial, single use syringe, etc.). The administration volume of a single unit dose may be no more than 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, or increments (e.g., 100 µL, 200 µL, 500 µL increments) therein. The compositions are suitably formulated for subdermal, preferably intralesional administration.

Where formulations having solid attributes (e.g., pellets or powders) are used, the amount of formulation injected/inserted will also depend, for example, on the size of the fibrotic tissue, the type and concentration treatment agent utilized, etc. Multiple pellets or doses of the composition can be administered at a single injection site. Regardless of the physical attributes of the formulation, multiple injection/insertion sites may be established within a single fibrotic tissue (e.g., a fibrous band, plaque, cord, nodule, etc.), with the number of injections depending on the size and/or shape of the fibrotic tissue as well as the type and/or concentration of the treatment agents that are used. Multiple fibrotic tissues or a single fibrotic tissue can be treated.

The compositions may also be provided in the form of a kit, which can contain the hyaluronidase and collagen-reducing agent in solid form, liquid or solvent for reconstitution and administration, and any equipment necessary for administration, such as for example, a syringe and needle. The kits may optionally comprise a package insert comprising instructional material for administering concurrently the hyaluronidase and collagen-reducing agent, and optionally one or more other active agents disclosed herein (e.g., selected from ancillary anti-fibrotic agents such as a steroid and an antimetabolite), to reduce or inhibit the development of fibrosis in a tissue, or to treat a collagen-mediated disorder (e.g., fibroproliferative disorder) in an individual.

In some embodiments, the hyaluronidase, collagen-reducing agent and optionally one or more ancillary agents disclosed herein are in the same container or in separate containers. Suitable containers include, for example, bottles, vials, bags and syringes. The container(s) may be formed from a variety of materials such as glass, plastic (such as polyvinyl chloride or polyolefin), or metal alloy (such as stainless steel or hastelloy). In some embodiments, a container holds the formulation and the label on, or associated with, the container may indicate directions for use. The kits may further include other materials desirable from a commercial and user standpoint, including other buffers, diluents, filters, needles, syringes, and package inserts with instructional material for use.

In illustrative examples, the kits comprise a first medicament comprising a hyaluronidase, an optional pharmaceutically acceptable carrier, and a package insert comprising instructional material for co-administration of the first medicament with a second medicament (i.e., not contained in the kits) comprising a collagen-reducing agent and an optional pharmaceutically acceptable carrier for reducing or inhibiting the development of fibrosis in a tissue, or for treating a collagen-mediated disorder (e.g., a fibroproliferative disorder such as a fibromatosis), or for enhancing the efficacy of a collagen-reducing agent for reducing or inhibiting the development of fibrosis in a tissue, or for treating a collagen-mediated disorder (e.g., a fibroproliferative disorder such as a fibromatosis), wherein the first medicament and second medicament are formulated for co-administration to a site of disease associated with the collagen-mediated disorder, or a site of manifestation of symptom thereof. In some embodiments, the package insert comprises instructional material for co-administration of the first and second medicaments with at least one other medicament comprising an ancillary anti-fibrotic agent as for example disclosed herein and an optional pharmaceutically acceptable carrier.

In other illustrative examples, the kits comprise the first medicament and the second medicament, optionally together with a package insert comprising instructional material for co-administering the first medicament and the second medicament and optionally the third medicament.

In still other illustrative examples, the kits comprise the first, second and third medicaments, optionally together with a package insert comprising instructional material for co-administering the medicaments.

The compositions of the present disclosure are useful for reducing or inhibiting the development of fibrosis, or for treating a collagen-mediated disorder (e.g., a fibroproliferative disorder such as a fibromatosis). Thus in some embodiments, methods are provided for reducing or inhibiting the development of fibrosis in a tissue, or for treating a collagen-mediated disorder (e.g., a fibroproliferative disorder such as a fibromatosis) in a subject, wherein the methods comprise contacting the tissue with, or co-administering to the subject, a collagen-reducing agent and a hyaluronidase, optionally in combination with at least one ancillary anti-fibrotic agent as disclosed for example herein, in effective amounts to reduce or inhibit the development of fibrosis, or to treat the collagen-mediated disorder.

Representative collagen-mediated disorders include, but are not limited to, systemic sclerosis, systemic sclerosis-related pulmonary fibrosis, sarcoidosis, sarcoidosis-related pulmonary fibrosis, pulmonary fibrosis caused by infection, asbestos-induced pulmonary fibrosis, silica-induced pulmonary fibrosis, environmentally induced pulmonary fibrosis, radiation-induced pulmonary fibrosis, lupus-induced pulmonary fibrosis, drug-induced pulmonary fibrosis, and hypersensitivity pneumonitis, and/or any disorder ameliorated by modulating fibrosis and/or collagen accumulation in tissues. In some embodiments, the collagen-mediated disorder is selected from uterine fibroids, Dupuytren's disease, Peyronie's disease, frozen shoulder (adhesive capsulitis), keloids, tennis elbow (lateral epicondylitis), scarred tendon, glaucoma, herniated discs, adjunct to vitrectomy, hypertrophic scars, depressed scars such as those resulting from inflammatory acne, post-surgical adhesions, acne vulgaris, lipomas, and disfiguring conditions such as wrinkling, cellulite formation and neoplastic fibrosis. In specific embodiments, the collagen-mediated disorder is a fibroproliferative disorder, which may be selected from hypertrophic scar, hyperplastic scar, keloid scar, liver fibrosis, lung fibrosis, skin fibrosis, muscle fibrosis, kidney fibrosis, glomerulosclerosis, uterine fibrosis, radiation fibrosis, and fibromatoses. In specific embodiments, the fibroproliferative disorder is a fibromatosis including fascial fibromatoses such as adhesive capsulitis, Dupuytren's disease, Peyronie's disease and Ledderhose's disease.

In some embodiments, the collagen-reducing agent and hyaluronidase may be administered simultaneously or sequentially, together or separately, and in representative examples of this type, they are administered locally, for example by injection, insertion or implantation. Optionally, they may be administered simultaneously, e.g., administering a composition comprising both collagen-reducing agent and hyaluronidase or by applying two separate compositions at the same time. Alternatively, the collagen-reducing agent and hyaluronidase are administered separately. When administered separately, they may be administered in any order a suitable time apart. Suitably, when administered separately the hyaluronidase is administered first followed by the collagen-reducing agent, which may be administered a suitable time after the hyaluronidase, e.g., after no less than 5 minutes, and suitably within 48 hours, 24 hours, 6 hours, 2 hours, 1 hour, 30 minutes, 15 minutes, suitably within 15 minutes to 3 hours. It is conceivable that more than one administration of either the hyaluronidase and/or collagen-reducing agent will be desired. Various combinations may be employed, where the hyaluronidase is "A" and collagen-reducing agent is "B", as exemplified below:

A/B/A B/A/B B/B/A A/A/B B/A/A A/B/B B/
B/B/A B/B/A/B A/A/B/B A/B/A/B
A/B/B/A B/B/A/A B/A/B/A B/A/A/B B/B/B/A A/A/
A/B B/A/A/A A/B/A/A A/A/B/A A/B/B/B B/A/B/B
B/B/A/B.

In preferred embodiments, the collagen-reducing agent and hyaluronidase are administered simultaneously for reducing or inhibiting the development of fibrosis, or for treating a collagen-mediated disorder (e.g., a fibroproliferative disorder such as a fibromatosis). In representative examples of this type, the composition is formulated for local administration (e.g., injectable solution, sustained release composition or implant), which composition comprises an effective amount of a hyaluronidase (or configured to release an effective amount of hyaluronidase if, for example, the composition is a sustained release composition) in combination with an effective amount of a collagen-reducing agent and a pharmaceutically acceptable carrier.

In non-limiting examples of this type, the hyaluronidase is provided in an amount effective to depolymerize or otherwise degrade HA in the extracellular matrix of a fibrotic lesion, which changes the viscoelastic properties of the lesion to facilitate increased hydraulic conductance of the co-administered collagen-reducing agent, thereby improving the rate of penetration of the collagen-reducing agent into the lesion extracellular matrix. In some embodiments, the effective amount of hyaluronidase increases the hydraulic conductance or rate of penetration of a co-administered collagen-reducing agent by at least 10%, 20%, 30%, 40%, 50%, 60%, 70%, 80%, 90%, 100%, 200%, 300%, 400%, 500%, 600%, 700%, 800%, 900%, or 1000% as compared to the hydraulic conductance or rate of penetration of the collagen-reducing agent alone (i.e., in the absence of the hyaluronidase). In some embodiments, an effective amount of hyaluronidase increases the efficacy of a co-administered collagen-reducing agent by at least 10%, 20%, 30%, 40%, 50%, 60%, 70%, 80%, 90%, 100%, 200%, 300%, 400%, 500%%, 600%, 700%, 800%, 900%, or 1000% as compared to the efficacy of the collagen-reducing agent alone (i.e., in the absence of the hyaluronidase). The increased efficacy includes, but is not limited to, any one or more reduced mean time required to reduce the size or volume of the fibrotic lesion, reduced mean time required to shrink the fibrotic lesion, reduced mean time required to degrade the fibrotic lesion, reduced mean time required to change the viscoelastic properties of the fibrotic lesion, reduced mean time required to soften the fibrotic lesion, reduced mean time required to relax the fibrotic lesion, stretch, and reduced mean time required to eliminate at least a portion of the fibrotic lesion. In some embodiments, the reduced mean time obtained with the hyaluronidase corresponds to at less than 80%, 70%, 60%, 50%, 40%, 30%, 20% or 10% of the mean time obtained with the collagen-reducing agent alone (i.e., in the absence of the hyaluronidase).

Suitably, the hyaluronidase is administered in an amount corresponding to about 10 U to about $2 \times 10^4$ U (and all integer units in between), about $1 \times 10^2$ U to about $1 \times 10^4$ U (and all integer units in between), about $4 \times 10^2$ U to about $5 \times 10^3$ U (and all integer units in between), about $6 \times 10^2$ U to about $4 \times 10^3$ U (and all integer units in between), about $8 \times 10^2$ U to about $3 \times 10^3$ U (and all integer units in between), about $1 \times 10^3$ U to about $2 \times 10^3$ U (and all integer units in between), or about $1.2 \times 10^3$ U to about $1.8 \times 10^3$ U (and all integer units in between). In illustrative examples of this type, the hyaluronidase is administered in an amount of about 0.01 mg to about 20 mg (and all one-hundredth milligram units in between), about 0.05 mg to about 10 mg (and all one-hundredth milligram units in between), about 0.1 mg to about 5 mg (and all one-tenth milligram units in between), about 0.2 mg to about 4 mg (and all one-tenth milligram units in between), about 0.3 mg to about 3 mg (and all one-tenth milligram units in between), or about 0.4 mg to about 2 mg (and all one-tenth milligram units in between). In specific embodiments, about $1.2 \times 10^2$ U to about $1.8 \times 10^2$ U (and all integer units in between) or about 0.04 mg to about 0.2 mg (and all one-tenth milligram units in between) of hyaluronidase is administered per cm$^3$ of fibrotic tissue to be treated.

The collagen-reducing agent is typically provided in an amount effective to reduce the size or volume of the fibrotic lesion, shrink the fibrotic lesion, degrade the fibrotic lesion, to change the viscoelastic properties of the fibrotic lesion, to soften the fibrotic lesion, to relax the fibrotic lesion, stretch and/or to eliminate at least a portion of the fibrotic lesion. In representative examples of this type, an effective amount of collagen-reducing agent is one that suppresses any increase in the amount of extracellular matrix such as collagen in fibrotic tissue, reduces the amount of extracellular matrix, and/or causes regeneration of normal tissue in fibrotic tissue.

The amount of extracellular matrix may be quantitatively determined by various methods such as, for example, without limitation, image analysis of a specially stained image of extracellular matrix or measurement of an extracellular matrix marker. For example, collagen may be quantitatively determined by measuring the amount of a collagen marker such as hydroxyproline, or by subjecting tissue to collagen staining (e.g., Masson trichrome staining, Azan staining, sirius red staining, Elastica van Gieson staining, etc.) and carrying out an image analysis. The percentage reduction of extracellular matrix in fibrotic tissue may be for example at least 10%, at least 20%, at least 30%, at least 40%, at least 50%, at least 60%, at least 70% and, moreover, at least 75% compared with a case in which the composition of the present disclosure has not been administered. Here, the case in which the composition of the present disclosure has not been administered includes not only a case in which administration itself has not been carried out but also a case in which a vehicle alone, or a collagen-reducing agent in the absence of hyaluronidase has been administered, and a case in which a composition corresponding to the composition of the present disclosure except that it does not contain the active ingredient has been administered. Furthermore, regeneration of normal tissue may be evaluated by histological observation or by administration of labeled stem cells to fibrotic tissue and carrying out a tracking survey thereof.

In some embodiments, the collagen-reducing agent is a collagenase-producing agent such a plasminogen activator (e.g., tPA or uPA). Suitably, the plasminogen activator is administered in an amount corresponding to about $1 \times 10^5$ U to about $1 \times 10^8$ U (and all integer units in between), about $5 \times 10^5$ U to about $5 \times 10^7$ U (and all integer units in between), about $1 \times 10^6$ U to about $4 \times 10^7$ U (and all integer units in between), about $2 \times 10^6$ U to about $3 \times 10^7$ U (and all integer units in between), about $3 \times 10^6$ U to about $2 \times 10^7$ U (and all integer units in between), about $4 \times 10^6$ U to about $1 \times 10^7$ U (and all integer units in between). In representative examples of this type, the plasminogen activator is administered in an amount of about 0.1 mg to about 200 mg (and all one-tenth milligram units in between), about 0.5 mg to about 100 mg (and all one-tenth milligram units in between), about 1 mg to about 50 mg (and all one-tenth milligram units in between), about 2 mg to about 40 mg (and all one-tenth milligram units in between), about 3 mg to about 30 mg (and all one-tenth milligram units in between), about 4 mg to about 20 mg (and all one-tenth milligram units in between). In specific embodiments, about $4 \times 10^5$ U to about $1 \times 10^6$ U (and all integer units in between), or about 0.4 mg to about 2 mg (and all one-tenth milligram units in between) of plasminogen activator is administered per cm$^3$ of fibrotic tissue to be treated.

In other embodiments, the collagen-reducing agent is a collagenase. Suitably, the collagenase is administered in an amount corresponding to about $1 \times 10^2$ collagen digestion units (CDU) to about $1 \times 10^5$ CDU (and all integer CDUs in between). In some embodiments, the collagenase is administered in an amount corresponding to about $1 \times 10^2$ CDU, $2 \times 10^2$ CDU, $3 \times 10^2$ CDU, $4 \times 10^2$ CDU, $5 \times 10^2$ CDU, $6 \times 10^2$ CDU, $7 \times 10^2$ CDU, $8 \times 10^2$ CDU, $9 \times 10^2$ CDU, $1 \times 10^3$ CDU, $2 \times 10^3$ CDU, $3 \times 10^3$ CDU, $4 \times 10^3$ CDU, $5 \times 10^3$ CDU, $6 \times 10^3$ CDU, $7 \times 10^3$ CDU, $8 \times 10^3$ CDU, $9 \times 10^3$ CDU, $1 \times 10^4$ CDU, $1.1 \times 10^4$ CDU, $1.2 \times 10^4$ CDU, $1.4 \times 10^4$ CDU or $1.5 \times 10^4$ CDU. In illustrative examples of this type, the collagenase is administered in an amount of about 0.1 mg to about 100 mg (and all one-tenth milligram units in between), about 0.2 mg to about 50 mg (and all one-tenth milligram units in between), about 0.3 mg to about 20 mg (and all one-tenth milligram units in between), about 0.4 mg to about 10 mg (and all one-tenth milligram units in between). In specific embodiments, the collagenase is administered in an amount of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or about 10 mg. In specific embodiments, about 10 CDU to about $1 \times 10^4$ CDU (and all integer CDUs in between), or about 0.1 mg to about 1 mg (and all one-tenth milligram units in between) of collagenase is administered per cm$^3$ of tissue to be treated.

In some embodiments, the collagen-reducing agent is administered in an amount significantly below (e.g., 0.01 to 0.5 times) the dose of collagen-reducing agent that would be required to achieve therapeutic efficacy in the absence of the hyaluronidase. In illustrative examples of this type, the collagen-reducing agent is a collagenase-producing agent (e.g., a plasminogen activator such as tPA) and the collagenase-producing agent is administered in an amount of about 2 mg to about 5 mg (and all one-tenth milligram units in between). In other illustrative examples, the collagen-reducing agent is a collagenase and the collagenase is administered in an amount of about 0.01 to 0.5 mg or 0.05 to 0.2 mg (and all one-tenth milligram units in between). In these embodiments, the respective doses of collagen-reducing agent and hyaluronidase may be synergistically effective doses.

The combination therapy of the present disclosure, which comprises a collagen-reducing agent and a hyaluronidase, optionally together with one or more ancillary anti-fibrotic agents, may be administered in a single dose or in multiple doses. One skilled in the art can readily determine an appropriate dosage regimen for administering the combination therapy of the present disclosure to a given subject. For example, the combination therapy can be administered to the subject once, such as by a single injection or deposition at or near the fibrosis. Alternatively, the combination therapy can be administered to a subject multiple times, for example daily, twice weekly, weekly, fortnightly, or at 3-week, 4-week, 5-week, 6-week, 2-month, 3-month, 4-month, 5-month, 6-month, or yearly intervals. Where multiple administrations are provided, in order to improve treatment efficacy or to inhibit disease progression or recurrence, the treated subject may be administered 2, 3, 4, 5, 6 or more administrations of the combination therapy. Alternatively, continuous treatment may be provided by low-dose releasing sustained or delayed intermittent release implant or patch. Alternatively, repeat doses may be initiated by signs of disease progression or recurrence.

In addition to their use in treating collagen-mediated disorders (e.g., fibroproliferative disorders such as fibromatoses), the compositions of the present disclosure are useful for the dissociation of tissue into individual cells and cell clusters as is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. In general, the composition of the present disclosure is useful for any application where the removal of cells or the modification of an extracellular matrix, is desired.

EMBODIMENTS OF THE DISCLOSURE

1. A pharmaceutical composition, suitably for use in reducing or inhibiting the development of fibrosis in a tissue, or in treating a collagen-mediated disorder (e.g., a fibroproliferative disorder such as a fibromatosis), the composition comprising, consisting or consisting essentially of a collagenase-producing agent and a hyaluronidase.
2. The composition of embodiment 2, wherein the collagenase-producing agent is selected from plasminogen and plasminogen activators (e.g., tissue plasminogen activator (tPA) and urokinase type plasminogen activator (uPA), kallikrein, Factor XII, streptokinase, saruplase, alteplase, reteplase, tenecteplase, anistreplase, monteplase, lanoteplase, parniteplase, staphylokinase and recombinant forms and variants of plasminogen and components of the plasminogen-activating pathway), a nucleic acid molecule from which plasminogen or a plasminogen activator is expressible, or a cell comprising such a nucleic acid molecule.
3. The composition of embodiment 2 or embodiment 3, wherein the collagenase-producing agent and hyaluronidase are in effective amounts to facilitate at least one of; reducing the size or volume of the fibrosis or the fibrotic tissue; shrinkage of the fibrosis or the fibrotic tissue associated with the collagen-mediated disorder; degradation of the fibrosis or the fibrotic tissue associated with the collagen-mediated disorder; modulation of the viscoelastic properties of the fibrosis or the fibrotic tissue associated with the collagen-mediated disorder; softening of the fibrotic tissue associated with the collagen-mediated disorder; relaxation of the fibrotic tissue associated with the collagen-mediated disorder; stretching of the fibrotic tissue associated with the collagen-mediated disorder; or elimination of at least a portion the fibrotic tissue associated with the collagen-mediated disorder.
4. The composition of any one of embodiments 1 to 3, wherein the collagenase-producing agent is a plasminogen activator.
5. The composition of embodiment 4, wherein the plasminogen activator is as tissue plasminogen activator (tPA) or a urokinase type plasminogen activator (uPA).
6. The composition of embodiment 4 or embodiment 5, wherein the plasminogen activator is present in the composition at a concentration of about $1 \times 10^4$ U/mL to about $1 \times 10^7$ U/mL (and all integer concentrations in between), about $5 \times 10^4$ U/mL to about $5 \times 10^6$ U/mL (and all integer concentrations in between), about $1 \times 10^5$ U/mL to about $4 \times 10^6$ U/mL (and all integer concentrations in between), about $2 \times 10^5$ U/mL to about $3 \times 10^6$ U/mL (and all integer concentrations in between), about $3 \times 10^5$ U/mL to about $2 \times 10^6$ U/mL (and all integer concentrations in between), or about $4 \times 10^5$ U/mL to about $1 \times 10^6$ U/mL (and all integer concentrations in between).
7. The composition of any one of embodiments 4 to 6, wherein the plasminogen activator is in an amount corresponding to about $1 \times 10^5$ U to about $1 \times 10^8$ U (and all integer units in between), about $5 \times 10^5$ U to about $5 \times 10^7$ U (and all integer units in between), about $1 \times 10^6$ U to about $4 \times 10^7$ U (and all integer units in between), about $2 \times 10^6$ U to about $3 \times 10^7$ U (and all integer units in between), about $3 \times 10^6$ U to about $2 \times 10^7$ U (and all integer units in between), about $4 \times 10^6$ U to about $1 \times 10^7$ U (and all integer units in between) per single unit dose.
8. The composition of any one of embodiments 4 to 7, wherein the plasminogen activator is in an amount of about 0.1 mg to about 200 mg (and all one-tenth milligram units in between), about 0.5 mg to about 100 mg (and all one-tenth milligram units in between), about 1 mg to about 50 mg (and all one-tenth milligram units in between), about 2 mg to about 40 mg (and all one-tenth milligram units in between), about 3 mg to about 30 mg (and all one-tenth milligram units in between), about 4 mg to about 20 mg (and all one-tenth milligram units in between) per single unit dose.

9. The composition of any one of embodiments 1 to 8, wherein the hyaluronidase is animal-derived or recombinantly-produced.

10. The method of embodiment 9, wherein the hyaluronidase is selected from Amphadase, Hyalase, Hydase, Hylase, rHuPH20/Hylenex, Vitrase and Wydase.

11. The composition of any one of embodiments 1 to 10, wherein the hyaluronidase is present in the composition at a concentration of about 1 U/mL to about $2\times10^3$ U/mL (and all integer concentrations in between), about 10 U/mL to about $1\times10^3$ U/mL (and all integer concentrations in between), about 40 U/mL to about $5\times10^2$ U/mL (and all integer concentrations in between), about 60 U/mL to about $4\times10^2$ U/mL (and all integer concentrations in between), about 80 U/mL to about $3\times10^2$ U/mL (and all integer concentrations in between), about $1\times10^2$ U/mL to about $2\times10^2$ U/mL (and all integer concentrations in between), or about $1.2\times10^2$ U/mL to about $1.8\times10^2$ U/mL (and all integer concentrations in between).

12. The composition of any one of embodiments 1 to 11, wherein the hyaluronidase is in an amount corresponding to about 10 U to about $2\times10^4$ U (and all integer units in between), about $1\times10^2$ U to about $1\times10^4$ U (and all integer units in between), about $4\times10^2$ U to about $5\times10^3$ U (and all integer units in between), about $6\times10^2$ U to about $4\times10^3$ U (and all integer units in between), about $8\times10^2$ U to about $3\times10^3$ U (and all integer units in between), about $1\times10^3$ U to about $2\times10^3$ U (and all integer units in between), or about $1.2\times10^3$ U to about $1.8\times10^3$ U (and all integer units in between) per single unit dose.

13. The composition of any one of embodiments 1 to 12, wherein the hyaluronidase is in an amount of about 0.01 mg to about 20 mg (and all one-hundredth milligram units in between), about 0.05 mg to about 10 mg (and all one-hundredth milligram units in between), about 0.1 mg to about 5 mg (and all one-tenth milligram units in between), about 0.2 mg to about 4 mg (and all one-tenth milligram units in between), about 0.3 mg to about 3 mg (and all one-tenth milligram units in between), or about 0.4 mg to about 2 mg (and all one-tenth milligram units in between) per single unit dose.

14. The composition of any one of embodiments 1 to 13, wherein the molar ratio of plasminogen activator to hyaluronidase in the composition is from about 50:1 to 5:1 (and all integer ratios in between), about 40:1 to 5:1 (and all integer ratios in between), about 30:1 to 5:1 (and all integer ratios in between), about 20:1 to 5:1 (and all integer ratios in between), 50:1 to 10:1 (and all integer ratios in between), about 40:1 to 10:1 (and all integer ratios in between), about 30:1 to 10:1 (and all integer ratios in between), or about 20:1 to 10:1 (and all integer ratios in between).

15. The composition of any one of embodiments 1 to 14, further comprising at least one ancillary anti-fibrotic agent.

16. The composition of embodiment 15, wherein the at least one ancillary anti-fibrotic agent is selected from a steroid and an antimetabolite.

17. The composition of embodiment 16, wherein the steroid is a corticosteroid.

18. The composition of embodiment 16 or embodiment 17, wherein the steroid is selected from prednisone, prednisolone, methylprednisolone, beclomethasone, betamethasone, dexamethasone, fludrocortisone, hydrocortisone, triamcinolone, their derivatives, prodrugs and pharmaceutically acceptable salts, and combinations thereof.

19. The composition of any one of embodiments 16 to 18, wherein the steroid is triamcinolone, a triamcinolone derivative, a triamcinolone prodrug, or a pharmaceutically acceptable salt thereof.

20. The composition of any one of embodiments 16 to 19, wherein the steroid (e.g., a corticosteroid such as triamcinolone, a triamcinolone derivative, a triamcinolone prodrug or a pharmaceutically acceptable salt thereof) is present in the composition at a concentration of about 0.1 mg/mL to about 60 mg/mL (and all one-tenth unit concentrations in between), about 0.2 mg/mL to about 50 mg/ml (and all one-tenth unit concentrations in between), about 0.4 mg/ml to about 40 mg/ml (and all one-tenth unit concentrations in between), about 0.6 mg/mL to about 30 mg/mL (and all one-tenth unit concentrations in between), about 0.8 mg/mL to about 20 mg/mL (and all one-tenth unit concentrations in between), or about 1 mg/ml to about 10 mg/ml (and all one-tenth unit concentrations in between).

21. The composition of any one of embodiments 16 to 20, wherein the steroid (e.g., a corticosteroid such as triamcinolone, a triamcinolone derivative, a triamcinolone prodrug or a pharmaceutically acceptable salt thereof) is present in the composition in an amount of about 1 mg to about 600 mg (and all integer milligram units in between), 2 mg to about 500 mg (and all integer milligram units in between), about 4 mg to about 400 mg (and all integer milligram units in between), about 6 mg to about 300 mg (and all integer milligram units in between), about 8 mg to about 200 mg (and all integer milligram units in between), about 10 mg to about 100 mg (and all integer milligram units in between), or about 12 mg to about 80 mg (and all integer milligram units in between) per single unit dose.

22. The composition of any one of embodiments 16 to 21, wherein the molar ratio of hyaluronidase to steroid (e.g., a corticosteroid such as triamcinolone, a triamcinolone derivative, a triamcinolone prodrug or a pharmaceutically acceptable salt thereof) in the composition is from about 1:100000 to 1:10000 (and all integer ratios in between), about 1:80000 to 1:10000 (and all integer ratios in between), about 1:60000 to 1:10000 (and all integer ratios in between), about 1:40000 to 1:10000 (and all integer ratios in between), 1:100000 to 1:20000 (and all integer ratios in between), about 1:80000 to 1:20000 (and all integer ratios in between), about 1:60000 to 1:20000 (and all integer ratios in between), about 1:40000 to 1:20000 (and all integer ratios in between), about 1:50000 to 1:5000 (and all integer ratios in between), about 1:40000 to 1:5000 (and all integer ratios in between), about 1:30000 to 1:5000 (and all integer ratios in between), about 1:20000 to 1:5000 (and all integer ratios in between), 1:50000 to 1:10000 (and all integer ratios in between), about 1:40000 to 1:10000 (and all integer ratios in between), about 1:30000 to 1:10000 (and all integer ratios in between), or about 1:20000 to 1:10000 (and all integer ratios in between).

23. The composition of any one of embodiments 16 to 22, wherein the antimetabolite is selected from pyrimidine antagonists, folic acid antagonists, purine antagonists and deaminase inhibitors.

24. The composition of embodiment 23, wherein the antimetabolite is selected from 5-fluorouracil, foxuridine, cytarabine, capecitabine, gemcitabine, 6-mercaptopurine, 6-thioguanine, cladribine, fludarabine, nelarabine and pentostatin, their derivatives and pharmaceutically acceptable salts, and combinations thereof.

25. The composition of embodiment 23 or 24, wherein the antimetabolite is 5-fluorouracil, a 5-fluorouracil derivative, a 5-fluorouracil prodrug, or a pharmaceutically acceptable salt thereof.

26. The composition of any one of embodiments 16 to 25, wherein the antimetabolite (e.g., 5-fluorouracil, a 5-fluorouracil derivative, a 5-fluorouracil prodrug, or a pharmaceutically acceptable salt thereof) is present in the composition in an amount of about 0.1 mg to about 50 mg (and all one-tenth milligram units in between), about 0.2 mg to about 40 mg (and all one-tenth milligram units in between), about 0.4 mg to about 30 mg (and all one-tenth milligram units in between), about 0.6 mg to about 20 mg (and all one-tenth milligram units in between), about 0.8 mg to about 16 mg (and all one-tenth milligram units in between), about 1 mg to about 12 mg (and all one-tenth milligram units in between), or about 2 mg to about 10 mg (and all one-tenth milligram units in between) per single unit dose.

27. The composition of any one of embodiments 16 to 26, wherein the molar ratio of hyaluronidase to antimetabolite (e.g., 5-fluorouracil, a 5-fluorouracil derivative, a 5-fluorouracil prodrug, or a pharmaceutically acceptable salt thereof) in the composition is from about 1:10000 to 1:1000 (and all integer ratios in between), about 1:8000 to 1:1000 (and all integer ratios in between), about 1:6000 to 1:1000 (and all integer ratios in between), about 1:4000 to 1:1000 (and all integer ratios in between), 1:10000 to 1:2000 (and all integer ratios in between), about 1:8000 to 1:2000 (and all integer ratios in between), about 1:6000 to 1:2000 (and all integer ratios in between), about 1:4000 to 1:2000 (and all integer ratios in between), about 1:5000 to 1:500 (and all integer ratios in between), about 1:4000 to 1:500 (and all integer ratios in between), about 1:3000 to 1:500 (and all integer ratios in between), about 1:2000 to 1:500 (and all integer ratios in between), 1:5000 to 1:1000 (and all integer ratios in between), about 1:4000 to 1:1000 (and all integer ratios in between), about 1:3000 to 1:1000 (and all integer ratios in between), or about 1:2000 to 1:1000 (and all integer ratios in between).

28. The composition of any one of embodiments 1 to 26, further comprising a buffering agent suitable to adjust the pH of the composition to a pH of about 5 to 8.

29. The composition of embodiment 28, wherein the buffering agent provides a pH selected from 5.5, 5.6, 5.7, 5.8, 5.9, 60, 6.1, 6.2, 6.3, 6.4, 6.5, 6.6, 6.7, 6.8, 6.9, 7.0, 7.1, 7.2, 7.3, 7.4, 7.5 and 7.6.

30. The composition of embodiment 28 or embodiment 29, wherein the buffering agent is suitable to adjust the pH of the composition to one approximating physiological blood.

31. The composition of any one of embodiments 28 to 30, wherein the buffering agent is an alkaline buffering agent, representative examples of which include amino acids, alkaline metal salts of amino acids, aluminum hydroxide, aluminum hydroxide/magnesium carbonate/calcium carbonate co-precipitate, aluminum magnesium hydroxide, aluminum hydroxide/magnesium hydroxide co-precipitate, aluminum hydroxide/sodium bicarbonate coprecipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tefrasodium pyrophosphate, tripotassium phosphate, trisodium phosphate, and frometamol. In certain embodiments, the alkaline buffering agent is selected from bicarbonates, including for example sodium bicarbonate, magnesium bicarbonate and calcium bicarbonate.

32. The composition of embodiment 31, wherein the buffering agent is selected from sodium bicarbonate, magnesium bicarbonate and calcium bicarbonate 33. The composition of any one of embodiments 1 to 32, further comprising a substance that reduces a fibrotic stimulus as an active ingredient, and/or that is used in combination with such a substance.

34. The composition of embodiment 33, wherein the substance that reduces a fibrotic stimulus is selected from an antioxidant, a blood circulation promoter, an anti-inflammatory drug, an antiviral drug, an antibiotic, an antiparasitic agent, a liver protection drug, a choleretic drug, and an apoptosis suppressor.

35. The composition of any one of embodiments 1 to 34, further comprising a pharmaceutically acceptable carrier.

36. The composition of any one of embodiments 1 to 35, which is in the form of a liquid composition.

37. The composition of any one of embodiments 1 to 36, which is formulated for subdermal, preferably intralesional administration.

38. The composition of any one of embodiments 1 to 37, which is formulated for direct injection into a tissue associated with fibrosis or fibrotic lesion associated with the collagen-mediated disorder.
39. A method for reducing or inhibiting the development of fibrosis in a tissue, suitably in a subject in need thereof, the method comprising, consisting or consisting essentially of contacting the tissue with a collagen-reducing agent and a hyaluronidase, to thereby reduce or inhibit the development of fibrosis in the tissue.
40. The method of embodiment 39 wherein the reduction or inhibition of fibrosis in the tissue or treatment of the collagen-mediated disorder is associated with at least one of: reduction in the size or volume of the fibrosis, shrinkage of the fibrosis; degradation of the fibrosis; modulation of the viscoelastic properties of the tissue; softening of the tissue, relaxation of the tissue, stretching of the tissue, and elimination of at least a portion the fibrosis in the tissue.
41. A method for treating a collagen-mediated disorder (e.g., a fibroproliferative disorder such as a fibromatosis) in a subject, the method comprising, consisting or consisting essentially of administering to the subject a collagen-reducing agent and a hyaluronidase in effective amounts to treat the collagen-mediated disorder, wherein the collagen-reducing agent and hyaluronidase are co-administered to a site of disease associated with the collagen-mediated disorder, or a site of manifestation of symptom thereof.
42. The method of embodiment 41, wherein the amounts of collagen-reducing agent and hyaluronidase are effective for reducing the size or volume, shrinking, degrading, changing the viscoelastic properties of, softening, relaxing, stretching, or eliminating at least a portion of, a fibrotic lesion associated with the collagen-mediated disorder.
43. The method of embodiment 41 or embodiment 42, wherein the collagen-reducing agent and hyaluronidase are administered in synergistically effective amounts.
44. The method of any one of embodiments 39 to 43, wherein the collagen-reducing agent is a collagen degradation agent, a suppressor of collagen production by collagen-producing cells, or a suppressor of a collagen degradation inhibitor.
45. The method of embodiment 44, wherein the collagen degradation agent is selected from a collagenase and a collagenase-producing agent.
46. The method of embodiment 45, wherein the collagenase is selected from bacterial collagenases such as *Clostridium histolyticum* (CCH) and mammalian matrix metalloproteinases (MMP) such as MMP1, MMP2, MMP3, MMP7, MMP8, MMP9, MMP10, MMP11, MMP12, MMP13, and MMP14.
47. The method of embodiment 45, wherein the collagenase-producing agent is selected from plasminogen and plasminogen activators (e.g., tissue plasminogen activator (tPA) and urokinase type plasminogen activator (uPA), kallikrein, Factor XII, streptokinase, saruplase, alteplase, reteplase, tenecteplase, anistreplase, monteplase, lanoteplase, parniteplase, staphylokinase and recombinant forms and variants of plasminogen and components of the plasminogen-activating pathway), a nucleic acid molecule from which plasminogen or a plasminogen activator is expressible, or a cell comprising such a nucleic acid molecule.
48. The method of embodiment 47, wherein the collagenase-producing agent is a plasminogen activator (e.g., a tPA such as alteplase) and the plasminogen activator is administered or contacted with the tissue in an amount corresponding to about $1\times10^5$ U to about $1\times10^8$ U (and all integer units in between), about $5\times10^5$ U to about $5\times10^7$ U (and all integer units in between), about $1\times10^6$ U to about $4\times10^7$ U (and all integer units in between), about $2\times10^6$ U to about $3\times10^7$ U (and all integer units in between), about $3\times10^6$ U to about $2\times10^7$ U (and all integer units in between), or about $4\times10^6$ U to about $1\times10^7$ U (and all integer units in between).
49. The method of embodiment 47 or embodiment 48, wherein the plasminogen activator is administered or contacted with the tissue in an amount of about 0.1 mg to about 200 mg (and all one-tenth milligram units in between), about 0.5 mg to about 100 mg (and all one-tenth milligram units in between), about 1 mg to about 50 mg (and all one-tenth milligram units in between), about 2 mg to about 40 mg (and all one-tenth milligram units in between), about 3 mg to about 30 mg (and all one-tenth milligram units in between), about 4 mg to about 20 mg (and all one-tenth milligram units in between).
50. The method of any one of embodiments 47 to 49, wherein about $4\times10^5$ U to about $1\times10^6$ U (and all integer units in between), or about 0.4 mg to about 2 mg (and all one-tenth milligram units in between) of plasminogen activator is administered per $cm^3$ of fibrotic tissue to be treated.
51. The method of any one of embodiments 39 to 50, wherein the hyaluronidase is animal-derived or recombinantly-produced.
52. The method of embodiment 51, wherein the hyaluronidase is selected from Amphadase, Hyalase, Hydase, Hylase, rHuPH20/Hylenex, Vitrase and Wydase.
53. The method of any one of embodiments 39 to 52, wherein the hyaluronidase is administered or contacted with the tissue in an amount corresponding to about 10 U to about $2\times10^4$ U (and all integer units in between), about $1\times10^2$ U to about $1\times10^4$ U (and all integer units in between), about $4\times10^2$ U to about $5\times10^3$ U (and all integer units in between), about $6\times10^2$ U to about $4\times10^3$ U (and all integer units in between), about $8\times10^2$ U to about $3\times10^3$ U (and all integer units in between), about $1\times10^3$ U to about $2\times10^3$ U (and all integer units in between), or about $1.2\times10^3$ U to about $1.8\times10^3$ U (and all integer units in between).
54. The method of any one of embodiments 39 to 53, wherein the hyaluronidase is administered or contacted with the tissue in an amount of about 0.01 mg to about 20 mg (and all one-hundredth milligram units in between), about 0.05 mg to about 10 mg (and all one-hundredth milligram units in between), about 0.1 mg to about 5 mg (and all one-tenth milligram units in between), about 0.2 mg to about 4 mg (and all one-tenth milligram units in between), about 0.3 mg to about 3 mg (and all one-tenth milligram units in between), or about 0.4 mg to about 2 mg (and all one-tenth milligram units in between).
55. The method of any one of embodiments 39 to 54, wherein about $1.2\times10^2$ U to about $1.8\times10^2$ U (and all integer units in between) or about 0.04 mg to about 0.2 mg (and all one-tenth milligram units in between) of hyaluronidase is administered per $cm^3$ of fibrotic tissue to be treated.

56. The method of any one of embodiments 39 to 55, further comprising contacting the tissue with at least one ancillary anti-fibrotic agent.
57. The method of embodiment 56, wherein the at least one ancillary anti-fibrotic agent is selected from a steroid and an antimetabolite.
58. The method of embodiment 57, wherein the steroid is a corticosteroid, representative examples of which include prednisone, prednisolone, methylprednisolone, beclomethasone, betamethasone, dexamethasone, fludrocortisone, hydrocortisone, triamcinolone, their derivatives, prodrugs and pharmaceutically acceptable salts, and combinations thereof.
59. The method of embodiment 57 or embodiment 58, wherein the steroid is triamcinolone, a triamcinolone derivative, a triamcinolone prodrug, or a pharmaceutically acceptable salt thereof.
60. The method of any one of embodiment 57 to 59, wherein the steroid is a corticosteroid (e.g., triamcinolone, a triamcinolone derivative, a triamcinolone prodrug or a pharmaceutically acceptable salt thereof), and the corticosteroid is administered or contacted with the tissue in an amount of about 1 mg to about 600 mg (and all integer milligram units in between), 2 mg to about 500 mg (and all integer milligram units in between), about 4 mg to about 400 mg (and all integer milligram units in between), about 6 mg to about 300 mg (and all integer milligram units in between), about 8 mg to about 200 mg (and all integer milligram units in between), about 10 mg to about 100 mg (and all integer milligram units in between), or about 12 mg to about 80 mg (and all integer milligram units in between).
61. The method of any one of embodiments 57 to 60, wherein the antimetabolite is selected from pyrimidine antagonists, folic acid antagonists, purine antagonists and deaminase inhibitors.
62. The method of embodiment 61, wherein the antimetabolite is selected from 5-fluorouracil, foxuridine, cytarabine, capecitabine, gemcitabine, 6-mercaptopurine, 6-thioguanine, cladribine, fludarabine, nelarabine and pentostatin, their derivatives and pharmaceutically acceptable salts, and combinations thereof.
63. The method of embodiment 61 or embodiment 62, wherein the antimetabolite is 5-fluorouracil, a 5-fluorouracil derivative, a 5-fluorouracil prodrug, or a pharmaceutically acceptable salt thereof.
64. The method of any one of embodiment 57 to 63, wherein the antimetabolite (e.g., 5-fluorouracil, a 5-fluorouracil derivative, a 5-fluorouracil prodrug, or a pharmaceutically acceptable salt thereof) is administered or contacted with the tissue in an amount of about 0.1 mg to about 50 mg (and all one-tenth milligram units in between), about 0.2 mg to about 40 mg (and all one-tenth milligram units in between), about 0.4 mg to about 30 mg (and all one-tenth milligram units in between), about 0.6 mg to about 20 mg (and all one-tenth milligram units in between), about 0.8 mg to about 16 mg (and all one-tenth milligram units in between), about 1 mg to about 12 mg (and all one-tenth milligram units in between), or about 2 mg to about 10 mg (and all one-tenth milligram units in between).
65. The method of any one of embodiments 41 to 64, wherein the collagen-mediated disorder is a fibroproliferative disorder which is suitably selected from hypertrophic scar, hyperplastic scar, keloid scar, liver fibrosis, lung fibrosis, skin fibrosis, muscle fibrosis, kidney fibrosis, glomerulosclerosis, uterine fibrosis, radiation fibrosis, and fibromatoses.
66. The method of embodiment 65, wherein the collagen-mediated disorder is a fibromatosis.
67. The method of embodiment 66, wherein the fibromatosis is a fascial fibromatosis.
68. The method of embodiment 66 or embodiment 67, wherein the fibromatosis is adhesive capsulitis, Peyronie's disease, Ledderhose's disease or Dupuytren's disease.
69. The method of any one of embodiments 41 to 68, wherein the local administration of the collagen-reducing agent and hyaluronidase is by local injection (e.g., intralesional injection, subdermal injection, etc.).
70. The method of any one of embodiments 41 to 69, the further comprising administering to the subject an adjunctive surgical treatment.
71. The method of embodiment 70, wherein the adjunctive surgical treatment is selected from surgical fasciectomy, surgical fasciotomy, surgical dermofasciectomy and needle fasciotomy.
72. The method of any one of embodiments 41 to 71, comprising contacting the tissue or administering the composition of any one of claims 1 to 38.
73. Use of a collagen-reducing agent and a hyaluronidase, optionally in combination with at least one ancillary anti-fibrotic agent that is suitably selected from a steroid and an antimetabolite, in the manufacture of a medicament for reducing or inhibiting the development of fibrosis in a tissue, or for treating a collagen-mediated disorder (e.g., a fibroproliferative disorder such as a fibromatosis).
74. Use of a hyaluronidase for enhancing the treatment efficacy of a collagen-reducing agent, optionally in combination with at least one ancillary anti-fibrotic agent that is suitably selected from a steroid and an antimetabolite, for reducing or inhibiting the development of fibrosis in a tissue, or for treating a collagen-mediated disorder (e.g., a fibroproliferative disorder such as a fibromatosis).
75. Use of a hyaluronidase, optionally in combination with at least one ancillary anti-fibrotic agent that is suitably selected from a steroid and an antimetabolite, for enhancing the efficacy of a collagen-reducing agent for reducing or inhibiting the development of fibrosis in a tissue, or for treating a collagen-mediated disorder (e.g., a fibroproliferative disorder such as a fibromatosis).
76. The method or use according to any preceding embodiment, wherein the collagen-reducing agent and hyaluronidase are formulated for local administration to a site of disease (e.g., lesion) associated with the collagen-mediated disorder, or a site of manifestation of symptom thereof.
77. The method or use according to any preceding embodiment, wherein the at least one ancillary anti-fibrotic agent (e.g., steroid and/or an antimetabolite) is independently formulated for local administration or systemic administration (e.g., orally, parenterally, intravenously, intradermally, subcutaneously, or topically, including transdermally).
78. A kit comprising a first medicament comprising a hyaluronidase, an optional pharmaceutically acceptable carrier, and a package insert comprising instructional material for co-administration of the first medicament with a second medicament comprising a collagen-reducing agent and an optional pharmaceutically acceptable carrier for reducing or inhibiting the development of fibrosis in a tissue, or for treating a collagen-mediated disorder (e.g., a fibroproliferative disorder such as a fibromatosis), or for enhancing the efficacy of a collagen-reducing agent for reducing or inhibiting the development of fibrosis in a tissue, or for treating a collagen-mediated disorder (e.g., a fibroproliferative disorder such as a fibromatosis, wherein the first medicament and second medicament are formulated for co-administration to a site of disease associated with the collagen-mediated disorder, or a site of manifestation of symptom thereof.

79. The kit of embodiment 78, wherein the package insert comprises instructional material for co-administration of the first and second medicaments with at least one other medicament comprising an ancillary anti-fibrotic agent that is suitably selected from a steroid and an antimetabolite, and an optional pharmaceutically acceptable carrier, wherein the ancillary anti-fibrotic agent is selected from a steroid and an antimetabolite.

80. A kit comprising a first medicament comprising a hyaluronidase and an optional pharmaceutically acceptable carrier, and a second medicament comprising a collagen-reducing agent and an optional pharmaceutically acceptable carrier for reducing or inhibiting the development of fibrosis in a tissue, or for treating a collagen-mediated disorder (e.g., a fibroproliferative disorder such as a fibromatosis).

81. The kit of embodiment 80, further comprising a package insert comprising instructional material for co-administering the first medicament and the second medicament for reducing or inhibiting the development of fibrosis in a tissue, or for treating a collagen-mediated disorder (e.g., a fibroproliferative disorder such as a fibromatosis), wherein the first medicament and second medicament are formulated for co-administration to a site of disease associated with the collagen-mediated disorder, or a site of manifestation of symptom thereof.

82. The kit of embodiment 81, wherein the package insert comprises instructional material for co-administration of the first and second medicaments with at least one other medicament comprising an ancillary anti-fibrotic agent that is suitably selected from a steroid and an antimetabolite and an optional pharmaceutically acceptable carrier.

83. A kit comprising a first medicament comprising a hyaluronidase and an optional pharmaceutically acceptable carrier, a second medicament comprising a collagen-reducing agent and an optional pharmaceutically acceptable carrier for reducing or inhibiting the development of fibrosis in a tissue, or for treating a collagen-mediated disorder (e.g., a fibroproliferative disorder such as a fibromatosis), and at least one other medicament comprising an ancillary anti-fibrotic agent that is suitably selected from a steroid and an antimetabolite and an optional pharmaceutically acceptable carrier, wherein the first and second medicaments are formulated for co-administration to a site of disease associated with the collagen-mediated disorder, or a site of manifestation of symptom thereof, and wherein the at least one other medicament is formulated for co-administration with the first and second medicaments.

84. The kit of embodiment 83, further comprising a package insert comprising instructional material for co-administering the first medicament, second medicament and the at least one other medicament for treating the collagen-mediated disorder.

85. The kit of any one of embodiments 78 to 84, wherein the medicaments are provided in a single composition.

86. The kit of any one of embodiments 78 to 84, wherein the medicaments are provided in separate compositions.

87. The kit of any one of embodiments 78 to 86, wherein the collagen-reducing agent, hyaluronidase and/or ancillary anti-fibrotic agent-containing compositions are in liquid form.

88. An article of manufacture for reducing or inhibiting the development of fibrosis in a tissue, or for treating a collagen-mediated disorder (e.g., a fibroproliferative disorder such as a fibromatosis), comprising, consisting or consisting essentially of the composition of any one of embodiments 1 to 38.

89. The article of manufacture of embodiment 88, which is a single use vial.

90. The article of manufacture of embodiment 88, which is a single use syringe.

In order that the disclosure may be readily understood and put into practical effect, particular preferred embodiments will now be described by way of the following non-limiting examples.

EXAMPLES

Example 1

Treatment of Dupuytren's Disease Using tPA in Combination with Hyaluronidase

Five subjects suffering from Dupuytren's disease were each treated with a single injection of a composition comprising 10 mg of ALTEPLASE (tPA) dissolved in 10 mL of HYALASE (1 ampoule). The composition also contained 40 mg KENACORT A40 (triamcinolone acetonide), 3 drops of 5-fluorouracyl (5-FU) (ancillary anti-fibrotic agents) and 120 mg sodium bicarbonate. Prior to injection, a local anesthetic (1% lignocaine solution containing sodium bicarbonate (8.4%) at a lignocaine to sodium bicarbonate ratio of 4:1) was applied to the area of the skin to be injected to reduce patient discomfort.

Using a 0.5-inch, 25 or 27 gauge needle, 5-10 mL of the composition was injected either directly into the visible cord (e.g., 10 mL) or partially into the cord (e.g., 5 mL) and the remainder (e.g., 5 mL) into the surrounding fascia. Patients were free to go home without the need for splinting or isolation of the hand or affected fingers. However, patients were requested to massage and extend the treated digit as often as possible.

Figure 2:
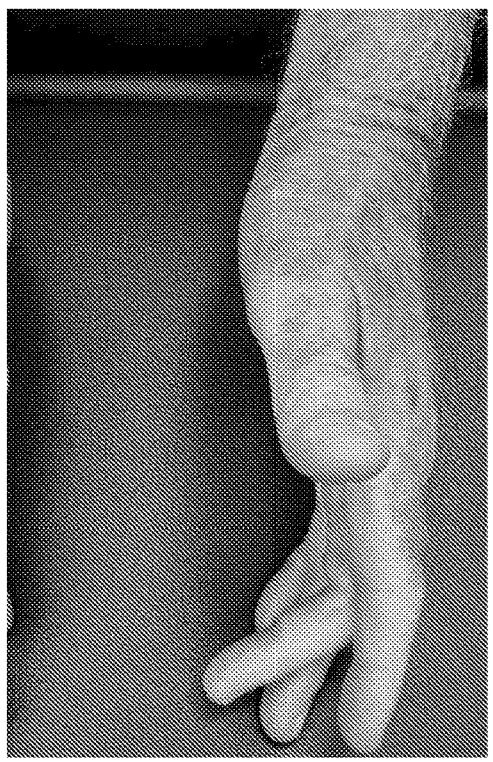
FIG. 2 is a photographic representation showing the results of treating another Dupuytren's disease patient with an embodiment of the composition of the present disclosure. A. Side view of the patient's contracted finger is shown prior to treatment with the composition. B. Perspective view of the patient's contracted finger is shown prior to treatment with the composition. C. Side view of the patient's finger is shown two days after intralesional injection of the composition. D. Perspective view of the patient's finger is shown two days after intralesional injection of the composition. An about 30-degree improvement in flexion of the diseased finger was obtained using this treatment.
Figure 2:
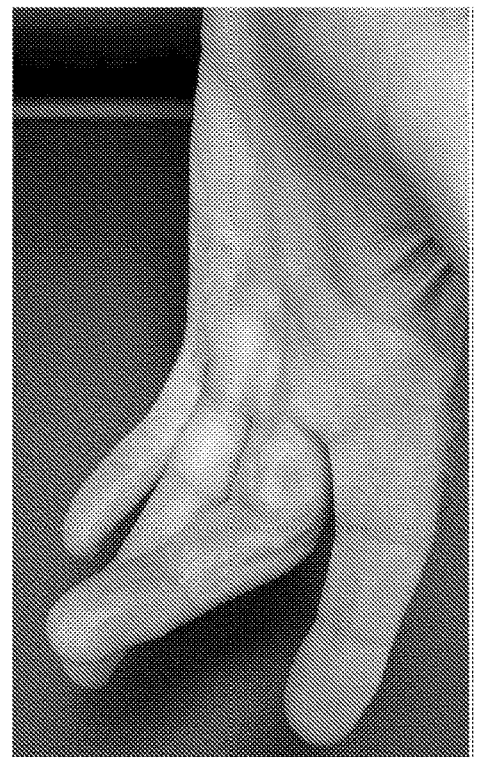
Figure 2:
Figure 2:
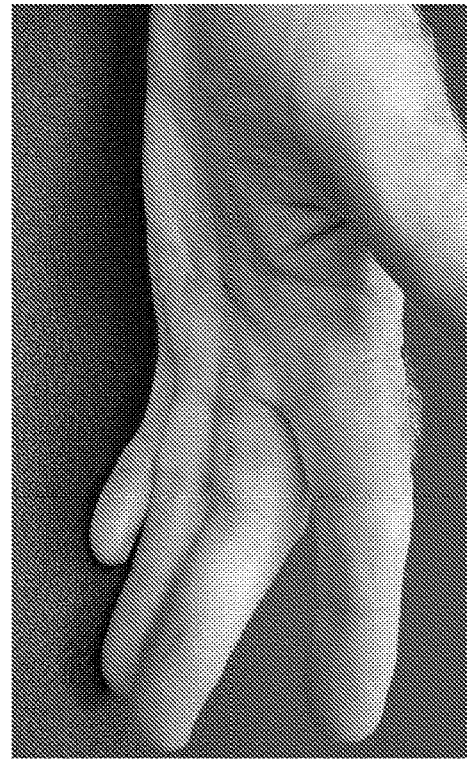

Following this treatment regimen, HYALASE was found to significantly reduce the mean time required to observe discernible reduction in volume of the fibromatosis, reduction of contracture and improvement in the range of motion in patients with Dupuytren's disease, from about 4-6 weeks when ALTEPLASE is administered on its own, to about 2-3 days when ALTEPLASE is co-administered with HYALASE ("combination treatment"). Representative results are shown in FIGS. 1 and 2 for two different patients.

Notably, the combination treatment achieved an average reduction in the volume of fibrotic tissue of about 80% after only 2-3 days post injection and an average improvement of at least 20-30 degrees in flexion of a diseased digit, which is much earlier than the 4-6 weeks required to obtain similar effects with ALTEPLASE alone. Additionally, the combination treatment resulted in a marked (on average about 30-50%) reduction in fibrotic tissue, including in the joints of the diseased fingers, which previously limited flexion and extension of phalanges connected to the joint. A disappearance or significant reduction of nodules was also observed, together with pronounced softening of the skin.

Figure 3:
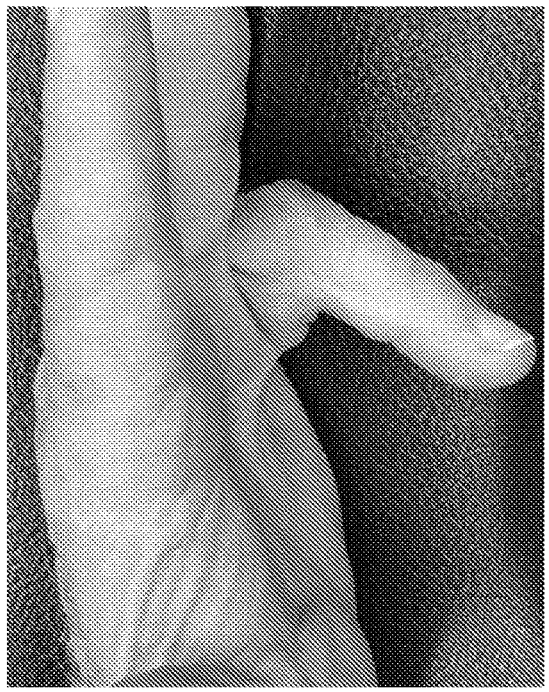
FIG. 3 is a photographic representation showing the results of two intralesional injections, spaced two weeks apart, into the cord of Dupuytren's disease patient with an embodiment of the composition of the present disclosure. A. Side view of the patient's contracted finger is shown prior to treatment with the composition. B. Frontal view of the patient's contracted finger is shown prior to treatment with the composition. C. Side view of the patient's finger is shown two days after a first intralesional injection of the composition. D. Frontal view of the patient's finger is shown two days after a first intralesional injection of the composition. E. Side view of the patient's finger is shown two days after a second intralesional injection of the composition. D. Frontal view of the patient's finger is shown two days after a second intralesional injection of the composition. At least a 60-degree improvement in flexion of the diseased finger was obtained using two intralesional injections spaced two weeks apart. In addition, the treatment resulted in disappearance of nodules, as well as a significant (about 60%) decrease in the volume of fibrotic tissue, including in the joints of the patient, which previously limited flexion and extension of phalanges connected to the joint.
Figure 3:
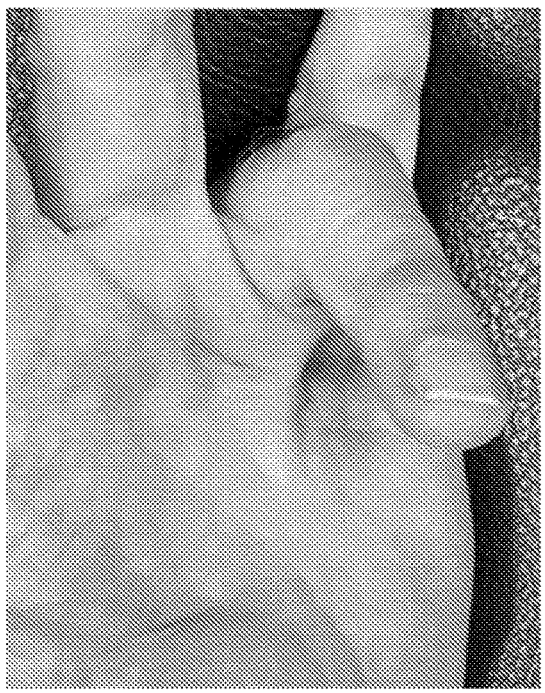
Figure 3:
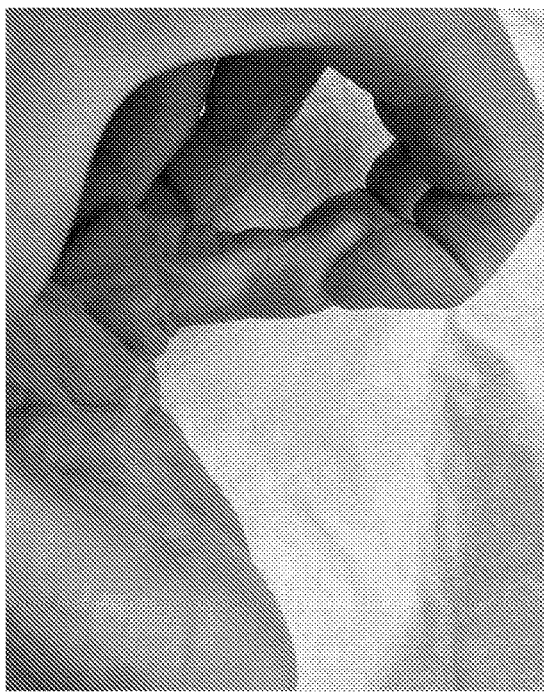
Figure 3:
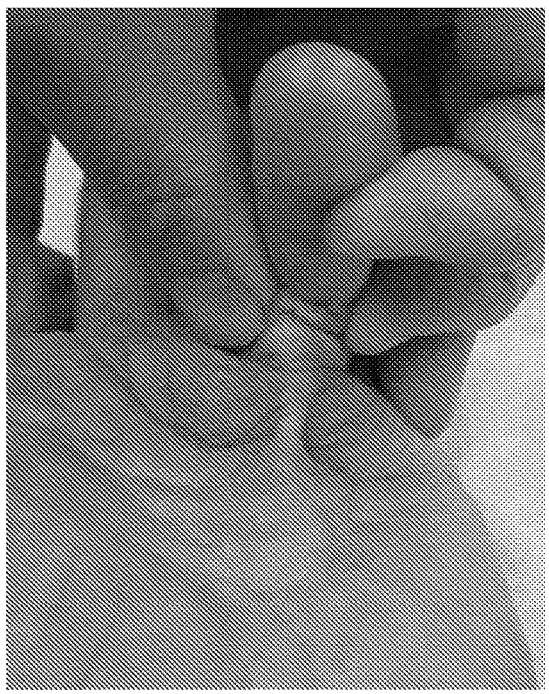
Figure 3:
Figure 3:
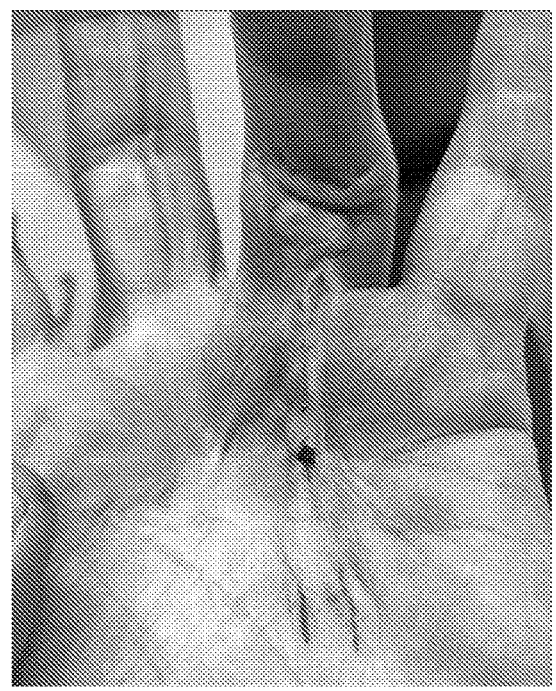
Figure 4:
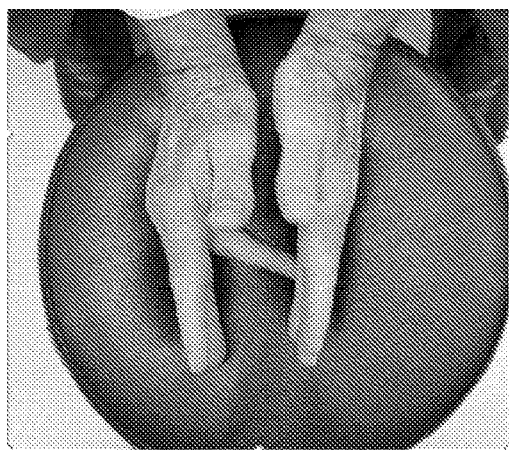
FIG. 4 is a photographic representation showing the results of two intralesional injections, spaced two weeks apart, into the cord of another Dupuytren's disease patient with an embodiment of the composition of the present disclosure. A. Side view of the patient's contracted finger is shown prior to treatment with the composition. B. Frontal view of the patient's contracted finger is shown prior to treatment with the composition. C. Side view of the patient's finger is shown two days after second intralesional injection of the composition. D. Frontal view of the patient's finger is shown two days after a second intralesional injection of the composition. At least a 60-degree improvement in flexion of the diseased finger was obtained using two intralesional injections spaced two weeks apart. In addition, the treatment resulted in disappearance of nodules, as well as a significant (about 60%) decrease in the volume of fibrotic tissue, including in the joints of the patient, which previously limited flexion and extension of phalanges connected to the joint.
Figure 4:
Figure 4:
Figure 4:

Further reduction in volume of the fibromatosis, reduction of contracture and improvement in the range of motion were obtained with further injections of the combination treatment at 2- to 3-weeks intervals. In two patients, for example, as shown in FIGS. 3 and 4, respectively, two administrations of the combination treatment spaced two weeks apart resulted in at least a 60-degree improvement in flexion of the diseased finger, disappearance of nodules, as well as a significant (greater than 60%) decrease in the volume of fibrotic tissue, including fibrotic tissue in the joints of the finger.

Another advantage of the combination treatment is that HYALASE significantly reduces the force and work required for injection of ALTEPLASE into the fibrotic lesion, leading to better control of the syringe needle, more effective intralesional dispersion of the ALTEPLASE, as well as improved patient safety and comfort.

Example 2

Treatment of Ledderhose's Disease Using Combination Treatment

A 59-year-old male, Ledderhose's disease patient presented with several nodules (fibromas) proximal to the medial plantar fascia. Pain associated with presence of these nodules limited walking and running. The composition according to Example 1 was injected into the nodules of the diseased foot, as follows:

Prior to injection, a local anesthetic (1% lignocaine solution containing sodium bicarbonate (8.4%) at a lignocaine to sodium bicarbonate ratio of 4:1) was applied to the area of the skin to be injected. Using a 0.5-inch, 25 gauge needle, about 5 mL of the composition was injected centrally into each nodule, followed by about 2.5 mL proximal and the remainder distally to the central aspect of the nodule. After the procedure, the patient was allowed to load the lower limb until tolerance level. The patient was discharged and requested to massage the plantar surface of the foot as often as possible over a 6-8-week period.

Of note, 3 days post-injection, the patient reported a substantial decrease in plantar pain with return to a more normal gait.

Figure 5:
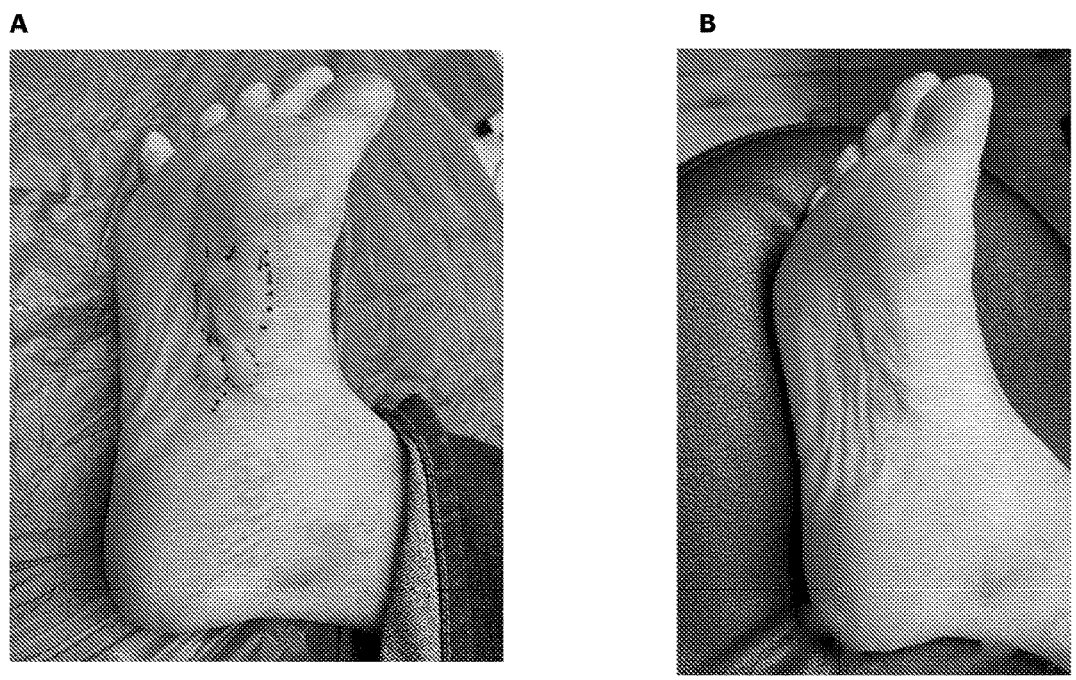
FIG. 5 is a photographic representation showing the results of treating a Ledderhose's disease patient with an embodiment of the composition of the present disclosure. A. Perspective view of the patient's right foot is shown prior to treatment with the composition. Nodules below the ball of the patient's foot are highlighted with a surgical pen. B. Perspective view of the patient's right foot is shown 8 weeks after a single intralesional injection of the composition. On visual appearance, the fibrous nodules almost disappeared using this treatment.

Four weeks post-injection, a significant reduction (>70%) in size and volume of the nodules, including disappearance of most nodules, was observed (FIG. 5), together with pronounced softening of the skin. The patient reported resolution of symptoms up to their last follow-up 2 months after the intervention.

The present combination treatment presents several advantages to Ledderhose's disease patients, including (1) returning rapidly to normal life, (2) reducing the costs of hospitalization and medical care, (3) avoiding painful scars, and (4) reducing recurrence of nodule formation.

Example 3

Treatment of Peyronie's Disease Using Combination Treatment

A 52-year-old male presented to clinic seeking treatment for Peyronie's disease. On exam, he was found to have a palpable dorsal plaque and >60-degree dorsal curvature of the penis. He was deemed an appropriate candidate for, and patient decided to proceed with, two intralesional injections, 6 weeks apart, as follows:

Prior to injection, a local anesthetic (1% lignocaine solution containing sodium bicarbonate (8.4%) at a lignocaine to sodium bicarbonate ratio of 4:1) was applied to the area of the skin at which the a palpable dorsal plaque (i.e., fibrotic lesion) was located. Complete detumescence was confirmed prior to injection. Using a 0.5-inch, 27-gauge needle, about 5 mL of the composition according to Example 1 was injected centrally into the plaque, followed by about 2.5 mL proximal and the remainder distally to the central aspect of the plaque. Pressure was then firmly applied for 1 to 3 minutes to achieve hemostasis.

Penile modeling was carried out by the patient at home starting when penile bruising or puncture pain subsides, usually 1-3 days post-injection. In particular, the patient was instructed to stretch the penis longitudinally until erect and bend the erect penis in the opposite direction of the penile curvature for 20-30 minutes per day over a 6-week period. The patient was also prescribed a course of VIAGRA to be taken on alternate days over this period and to have sexual activity as often as possible. At the completion of the period, the patient was exposed to a second injection cycle.

Figure 6:
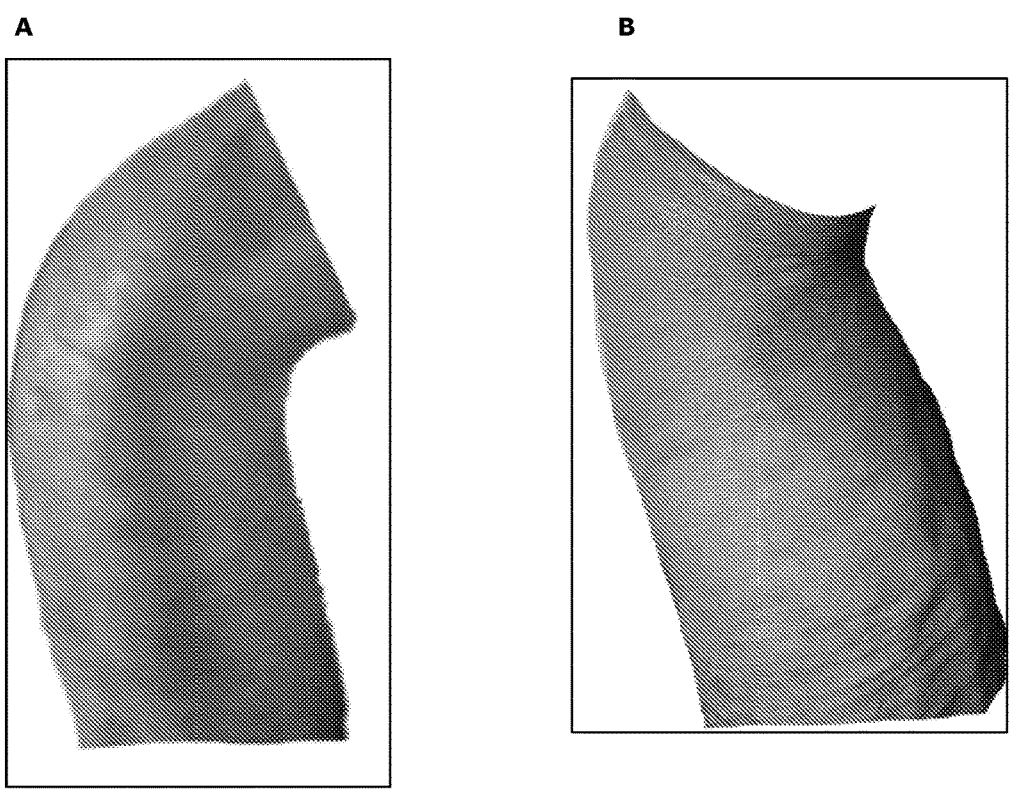
FIG. 6 is a photographic representation showing the results of treating a Peyronie's disease patient with an embodiment of the composition of the present disclosure. A. Side view of the patient's penis with >60-degree dorsal curvature is shown prior to treatment with the composition. B. Side view of the patient's penis after two intralesional injections of the composition, which were 6 weeks apart. A pronounced improvement in penile curvature of at least 40 degrees is shown. Additionally, the patient reported that there was no erectile pain and improved erectile quality following two injection cycle of the composition.

In a follow-up consultation 6 weeks after the second injection, a pronounced improvement in penile curvature of at least 40 degrees was observed, in which the dorsal plaque almost disappeared (FIG. 6). The patient reported no erectile pain and improved erectile quality.

The present combination treatment presents several advantages to Peyronie's disease patients, including (1) returning to normal sexual activity with reduced erectile pain, (2) reducing the costs of hospitalization and medical care, and (3) avoiding painful scars.

Example 4

Treatment of Keloid Scar Using Combination Treatment

A 44-year-old male presented to the clinic with a ~10 cm hard keloid scar on his left scapula, which was reported to be painful and itchy. The composition according to Example 1 was injected into an about 15×15 mm$^2$ treatment area of the keloid scar, as follows:

Prior to injection, a local anesthetic (1% lignocaine solution containing sodium bicarbonate (8.4%) at a lignocaine to sodium bicarbonate ratio of 4:1) was applied to the treatment area to be injected. Using a 0.5-inch, 27 gauge needle, about 5 mL of the composition was injected centrally into the treatment area, followed by about 2.5 mL proximal and the remainder distally to the central aspect of the treatment area. After the procedure, the patient was requested to massage the treated area with petroleum jelly 20-30 minutes per day over a 6-week period.

Figure 7:
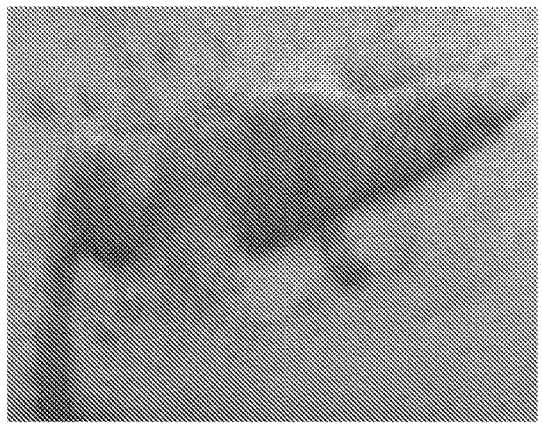
FIG. 7 is a photographic representation showing the results of treating a keloid scar with an embodiment of the composition of the present disclosure. A. Perspective view of the patient's keloid scar is shown prior to treatment with the composition. B. Perspective view of the patient's keloid scar is shown after treatment with the composition. A significant reduction in the volume of the keloid scar was observed, with growth of normal skin and significant relief of pain and irritation in the treatment area.
Figure 7:
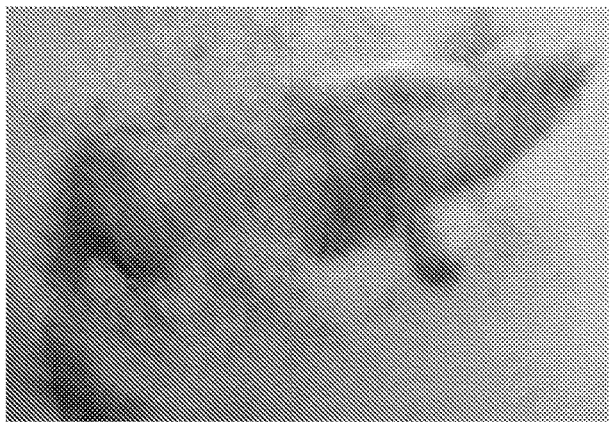

In a follow-up consultation 6 weeks post-injection, a significant reduction in the volume of the keloid scar was observed, with growth of normal skin and significant relief of pain and irritation in the treatment area (FIG. 7).

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the disclosure without limiting the disclosure to any one embodiment or specific collection of features. Those of skill in the art will therefore appreciate that, in light of the instant disclosure, various modifications and changes can be made in the particular embodiments exemplified without departing from the scope of the present disclosure. All such modifications and changes are intended to be included within the scope of the appended claims.

What is claimed is:

1. A pharmaceutical composition comprising:
a plasminogen activator in an amount of 1 mg to 50 mg per single unit dose, wherein the plasminogen activator is selected from saruplase, alteplase, reteplase, tenecteplase, anistreplase, monteplase and lanoteplase; and
a hyaluronidase in amount of 0.4 mg to 2 mg per single unit dose, wherein the hyaluronidase is selected from Amphadase, Hyalase, Hydase, Hylase, rHuPH20/Hylenex, Vitrase, and Wydase.

2. The pharmaceutical composition of claim 1, wherein the plasminogen activator is present in an amount of 3 mg to 30 mg per single unit dose.

3. The pharmaceutical composition of claim 1, wherein the plasminogen activator is alteplase; and
the hyaluronidase is Hyalase.

4. The pharmaceutical composition of claim 1, further comprising:
a steroid in an amount of 12 mg to 80 mg per single unit dose;
an antimetabolite in an amount of 2 mg to 10 mg per single unit dose; and
a buffering agent.

5. The pharmaceutical composition of claim 4, wherein the plasminogen activator is present in an amount of 3 mg to 30 mg per single unit dose.

6. The pharmaceutical composition of claim 4, wherein the
plasminogen activator is alteplase; and
the hyaluronidase is Hyalase.

7. The pharmaceutical composition of claim 1, further comprising:
a steroid in an amount of 12 mg to 80 mg per single unit dose, wherein the steroid is selected from prednisone, prednisolone, methylprednisolone, beclomethasone, betamethasone, dexamethasone, fludrocortisone, hydrocortisone, triamcinolone, derivatives thereof, prodrugs thereof, pharmaceutically acceptable salts thereof, and combinations thereof;
an antimetabolite in an amount of 2 mg to 10 mg per single unit dose, wherein the antimetabolite is selected from 5-fluorouracil, foxuridine, cytarabine, capecitabine, gemcitabine, 6-mercaptopurine, 6-thioguanine, cladribine, fludarabine, nelarabine, pentostatin, derivatives thereof, pharmaceutically acceptable salts thereof, and combinations thereof; and
sodium bicarbonate.

8. The pharmaceutical composition of claim 7, wherein the plasminogen activator is present in an amount of 3 mg to 30 mg per single unit dose.

9. The pharmaceutical composition of claim 1, further comprising:
a steroid in an amount of 12 mg to 80 mg per single unit dose, wherein the steroid is selected from prednisone, prednisolone, methylprednisolone, beclomethasone, betamethasone, dexamethasone, fludrocortisone, hydrocortisone, triamcinolone, derivatives thereof, prodrugs thereof, pharmaceutically acceptable salts thereof, and combinations thereof;
an antimetabolite in an amount of 2 mg to 10 mg per single unit dose, wherein the antimetabolite is selected from 5-fluorouracil, foxuridine, cytarabine, capecitabine, gemcitabine, 6-mercaptopurine, 6-thioguanine, cladribine, fludarabine, nelarabine, pentostatin, derivatives thereof, pharmaceutically acceptable salts thereof, and combinations thereof; and sodium bicarbonate,
wherein the plasminogen activator is alteplase a tissue plasminogen activator.

10. The pharmaceutical composition of claim 9, wherein the plasminogen activator is present in an amount of 3 mg to about 30 mg per single unit dose.

11. The pharmaceutical composition of claim 9, wherein the hyaluronidase is Hyalase.

12. A single use vial or syringe comprising the pharmaceutical composition of claim 1.

13. A single use vial or syringe comprising the pharmaceutical composition of claim 2.

14. A single use vial or syringe comprising the pharmaceutical composition of claim 4.

15. A single use vial or syringe comprising the pharmaceutical composition of claim 5.

16. A single use vial or syringe comprising the pharmaceutical composition of claim 7.

17. A single use vial or syringe comprising the pharmaceutical composition of claim 8.

18. A single use vial or syringe comprising the pharmaceutical composition of claim 9.

19. A single use vial or syringe comprising the pharmaceutical composition of claim 10.

20. A pharmaceutical composition comprising:
alteplase in an amount of 1 mg to 50 mg per single unit dose; and
Hyalase in amount of from 0.4 mg to 2 mg per single unit dose.

21. The pharmaceutical composition of claim 20, wherein the alteplase is present in an amount of 3 mg to 30 mg per single unit dose.

22. The pharmaceutical composition of claim 20, further comprising a steroid in an amount of 12 mg to 80 mg per single unit dose, wherein the steroid is selected from prednisone, prednisolone, methylprednisolone, beclomethasone, betamethasone, dexamethasone, fludrocortisone, hydrocortisone, triamcinolone, derivatives thereof, prodrugs thereof, pharmaceutically acceptable salts thereof, and combinations thereof.

23. The pharmaceutical composition of claim 21, wherein the corticosteroid is triamcinolone.

24. The pharmaceutical composition of claim 20, further comprising an antimetabolite in an amount of 2 mg to 10 mg per single unit dose, wherein the antimetabolite is selected from 5-fluorouracil, foxuridine, cytarabine, capecitabine, gemcitabine, 6-mercaptopurine, 6-thioguanine, cladribine, fludarabine, nelarabine, pentostatin, derivatives thereof, pharmaceutically acceptable salts thereof, and combinations thereof.

25. The pharmaceutical composition of claim 24, wherein the antimetabolite is 5-fluorouracyl.

26. A single use vial or syringe comprising the pharmaceutical composition of claim 20.

* * * * *